United States Patent
Gibson et al.

(10) Patent No.: US 10,758,683 B2
(45) Date of Patent: Sep. 1, 2020

(54) DRUG DELIVERY SYSTEM WITH TEMPERATURE-SENSITIVE CONTROL

(71) Applicant: AMGEN INC., Thousand Oaks, CA (US)

(72) Inventors: Scott R. Gibson, Granada Hills, CA (US); Mark Ka Lai Lee, Newbury Park, CA (US); Donald Busby, Thousand Oaks, CA (US); Stephanie Toy, Moorpark, CA (US); Suhas Krishna, Simi Valley, CA (US); Francisca Tan-Malecki, Westlake Village, CA (US); Ferry Tamtoro, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 272 days.

(21) Appl. No.: 14/913,928

(22) PCT Filed: Oct. 22, 2014

(86) PCT No.: PCT/US2014/061680
§ 371 (c)(1),
(2) Date: Feb. 23, 2016

(87) PCT Pub. No.: WO2015/061389
PCT Pub. Date: Apr. 30, 2015

(65) Prior Publication Data
US 2016/0354555 A1   Dec. 8, 2016

Related U.S. Application Data

(60) Provisional application No. 61/895,285, filed on Oct. 24, 2013.

(51) Int. Cl.
*A61M 5/44* (2006.01)
*A61M 5/162* (2006.01)
(Continued)

(52) U.S. Cl.
CPC ........ *A61M 5/445* (2013.01); *A61M 5/14216* (2013.01); *A61M 5/14248* (2013.01);
(Continued)

(58) Field of Classification Search
CPC .. A61M 2205/3368; A61M 2205/3306; A61M 2205/3313; A61M 2205/364;
(Continued)

(56) References Cited

U.S. PATENT DOCUMENTS 3,771,899 A   11/1973   Brumfield
5,037,396 A   8/1991   Streeter
(Continued)

FOREIGN PATENT DOCUMENTS

CA   2668672 A1   6/2008
JP   2010510867 A   4/2010
(Continued)

OTHER PUBLICATIONS

Office Action issued in Japanese Patent Application No. 2016-550468, dated Oct. 2, 2018 (translation enclosed).
(Continued)

*Primary Examiner* — Kevin C Sirmons
*Assistant Examiner* — Tezita Z Watts
(74) *Attorney, Agent, or Firm* — Marshall, Gerstein & Borun LLP

(57) ABSTRACT

A drug delivery system includes a reservoir and a drug delivery device coupled to the reservoir. The drug delivery device also may include at least one temperature-sensitive component and a lock having locked and unlocked states. The system further includes an output device, and a controller coupled to the lock and the output device. The controller may also include a temperature sensor, or may be coupled to the temperature sensor. The controller is programmed or configured to determine if the temperature of a
(Continued)

drug in the reservoir or of the temperature-sensitive component exceeds an upper limit or is below a lower limit, and to activate the lock in either event. The controller is also programmed or configured to determine, directly or indirectly, if the temperature subsequently is between the upper and lower limits, and to unlock lock as a consequence.

40 Claims, 9 Drawing Sheets

(51) Int. Cl.
  *A61M 5/315*   (2006.01)
  *A61M 5/20*   (2006.01)
  *A61M 5/142*   (2006.01)
  *A61M 5/172*   (2006.01)
  *A61M 5/31*   (2006.01)

(52) U.S. Cl.
  CPC ............ *A61M 5/162* (2013.01); *A61M 5/172* (2013.01); *A61M 5/2033* (2013.01); *A61M 5/3129* (2013.01); *A61M 5/31566* (2013.01); *A61M 2005/14252* (2013.01); *A61M 2205/0227* (2013.01); *A61M 2205/18* (2013.01); *A61M 2205/276* (2013.01); *A61M 2205/3306* (2013.01); *A61M 2205/3313* (2013.01); *A61M 2205/3368* (2013.01); *A61M 2205/364* (2013.01); *A61M 2205/3653* (2013.01); *A61M 2205/3673* (2013.01); *A61M 2205/50* (2013.01); *A61M 2205/502* (2013.01); *A61M 2205/581* (2013.01); *A61M 2205/587* (2013.01); *A61M 2205/8206* (2013.01)

(58) Field of Classification Search
  CPC .. A61M 2205/3673; A61M 2205/3653; A61M 2205/50; A61M 2205/502; A61M 2205/581; A61M 2205/587; A61M 2205/8206; A61M 2205/18; A61M 2205/276; A61M 5/14216; A61M 5/14248; A61M 5/162; A61M 5/172; A61M 5/3129; A61M 5/40; A61M 2205/0227
  See application file for complete search history.

(56) References Cited

U.S. PATENT DOCUMENTS

| | | | |
|---|---|---|---|
| 5,368,562 A | | 11/1994 | Blomquist et al. |
| 5,498,261 A | * | 3/1996 | Strul .................. A61M 25/104 606/29 |
| 5,814,020 A | | 9/1998 | Gross |
| 5,858,001 A | | 1/1999 | Tsals et al. |
| 5,957,895 A | | 9/1999 | Sage et al. |
| 6,131,570 A | * | 10/2000 | Schuster ............... A61M 15/00 128/203.26 |
| 6,236,809 B1 | | 5/2001 | Cassidy et al. |
| 6,480,257 B2 | | 11/2002 | Cassidy et al. |
| 6,656,158 B2 | | 12/2003 | Mahoney et al. |
| 6,656,159 B2 | | 12/2003 | Flaherty |
| 6,929,619 B2 | | 8/2005 | Fago et al. |
| 7,128,727 B2 | | 10/2006 | Flaherty et al. |
| 7,144,384 B2 | | 12/2006 | Gorman et al. |
| 7,381,201 B2 | | 6/2008 | Gilbert et al. |
| 7,658,737 B2 | | 2/2010 | Hartlaub et al. |
| 7,744,594 B2 | * | 6/2010 | Yamazaki ........... A61B 18/1492 604/96.01 |
| 8,118,790 B2 | | 2/2012 | Dacquay et al. |
| 8,337,453 B2 | | 12/2012 | Lind |
| 8,465,459 B2 | | 6/2013 | Nagel et al. |
| 8,622,991 B2 | | 1/2014 | Pesach et al. |
| 8,741,336 B2 | | 6/2014 | DiPierro et al. |
| 8,827,979 B2 | | 9/2014 | Pesach et al. |
| 8,922,367 B2 | | 12/2014 | Denny et al. |
| 8,961,458 B2 | | 2/2015 | Pesach et al. |
| 8,968,254 B2 | | 3/2015 | Pommerau et al. |
| 9,082,157 B2 | | 7/2015 | Gibson |
| 2005/0177137 A1 | | 8/2005 | Kipfer |
| 2007/0239381 A1 | | 10/2007 | Ginggen et al. |
| 2007/0268340 A1 | | 11/2007 | Dacquay et al. |
| 2008/0097379 A1 | | 4/2008 | Dacquay et al. |
| 2008/0097390 A1 | | 4/2008 | Dacquay et al. |
| 2008/0125700 A1 | * | 5/2008 | Moberg ............ A61M 5/14244 604/67 |
| 2008/0234625 A1 | | 9/2008 | Dacquay et al. |
| 2008/0281292 A1 | | 11/2008 | Hickingbotham et al. |
| 2008/0281297 A1 | * | 11/2008 | Pesach .................. A61M 5/158 604/890.1 |
| 2009/0012447 A1 | * | 1/2009 | Huitt ....................... G01F 15/02 604/28 |
| 2009/0036868 A1 | * | 2/2009 | Pinedjian ............... A61F 9/0017 604/506 |
| 2009/0177182 A1 | | 7/2009 | Hickingbotham et al. |
| 2009/0227979 A1 | | 9/2009 | Sanchez, Jr. |
| 2010/0057003 A1 | | 3/2010 | Dos Santos |
| 2010/0106083 A1 | | 4/2010 | Dacquay et al. |
| 2010/0106089 A1 | | 4/2010 | Santos et al. |
| 2010/0152676 A1 | | 6/2010 | Clements et al. |
| 2011/0054285 A1 | | 3/2011 | Searle et al. |
| 2011/0313351 A1 | | 12/2011 | Kamen et al. |
| 2012/0116197 A1 | | 5/2012 | Moberg et al. |
| 2013/0056888 A1 | * | 3/2013 | Holakovsky ...... A61M 15/0071 261/78.2 |
| 2013/0177455 A1 | * | 7/2013 | Kamen .................. G16H 20/17 417/313 |
| 2013/0338576 A1 | | 12/2013 | O'Connor et al. |
| 2013/0338635 A1 | | 12/2013 | O'Connor et al. |
| 2014/0010727 A1 | | 1/2014 | Jugl et al. |
| 2014/0054883 A1 | | 2/2014 | Lanigan et al. |
| 2014/0094770 A1 | | 4/2014 | Li et al. |
| 2014/0155679 A1 | | 6/2014 | Pesach et al. |
| 2014/0236076 A1 | | 8/2014 | Marshall et al. |
| 2014/0276545 A1 | * | 9/2014 | Krogh Andersen .... A61M 5/44 604/500 |
| 2014/0309622 A1 | | 10/2014 | Blomquist et al. |
| 2014/0330243 A1 | | 11/2014 | Kietzmann et al. |
| 2015/0011965 A1 | | 1/2015 | Cabiri |
| 2015/0051545 A1 | | 2/2015 | Henderson et al. |
| 2015/0051579 A1 | | 2/2015 | Chung et al. |
| 2015/0094660 A1 | | 4/2015 | Mandro et al. |
| 2015/0141918 A1 | | 5/2015 | Anderson et al. |
| 2015/0141919 A1 | | 5/2015 | Henderson et al. |
| 2015/0151044 A1 | | 6/2015 | Anderson et al. |
| 2015/0151047 A1 | | 6/2015 | Anderson et al. |
| 2015/0246179 A1 | | 9/2015 | Zur et al. |

FOREIGN PATENT DOCUMENTS

| | | |
|---|---|---|
| JP | 2010522012 A | 7/2010 |
| WO | WO-2008114218 A2 | 9/2008 |
| WO | WO-2013055873 A1 | 4/2013 |

OTHER PUBLICATIONS

Japanese Patent Application No. 2016-550468, Examiner's Decision of Rejection, dated Feb. 5, 2019.
European Patent Application No. 19152703.5, Extended European Search Report, dated May 27, 2019.
International Search Report for PCT/US2014/061680, dated Mar. 3, 2015.
Japanese Patent Application No. 2016-550468, Official Action dated Jun. 2, 2020 and translation thereof.

* cited by examiner

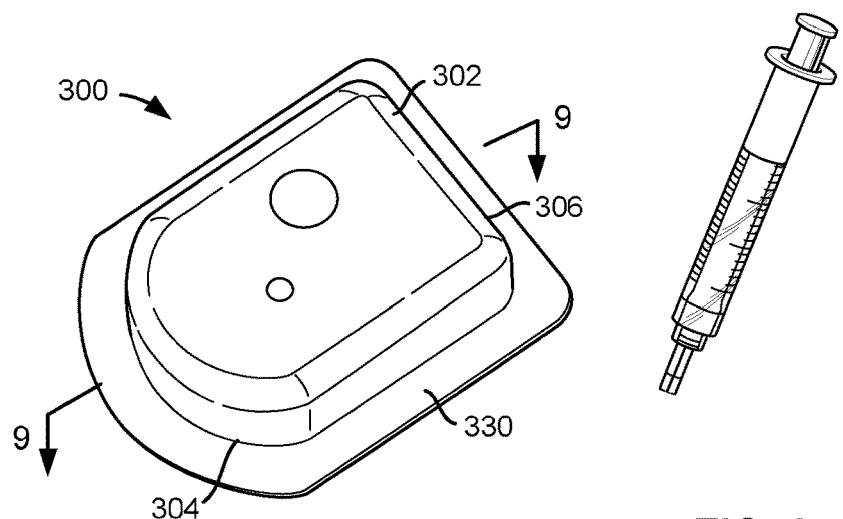
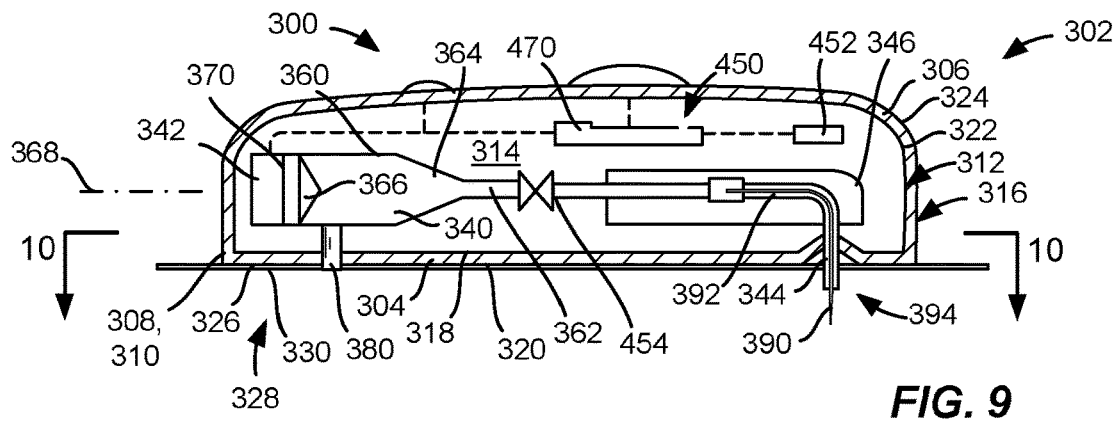
FIG. 8
FIG. 9
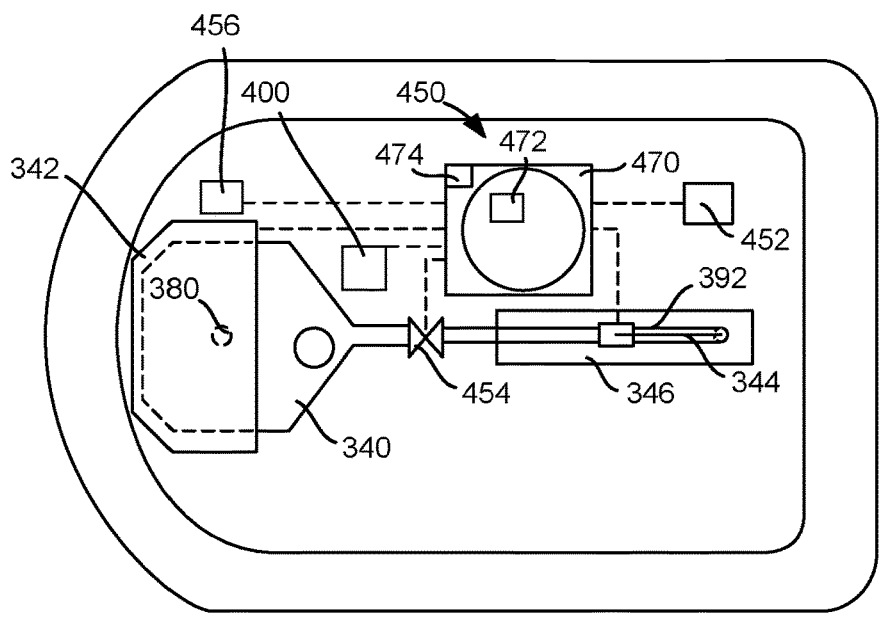
FIG. 10

DRUG DELIVERY SYSTEM WITH TEMPERATURE-SENSITIVE CONTROL

CROSS-REFERENCE TO RELATED APPLICATIONS

This is the US National Phase of International Patent Application No. PCT/US14/61680, having an international filing date of Oct. 22, 2014, and which claims the priority benefit of U.S. Provisional Application No. 61/895,285, filed Oct. 24, 2013. The entire contents of each of the foregoing is expressly incorporated herein by reference.

FIELD OF THE DISCLOSURE

This patent is directed to a drug delivery system and, in particular, to a drug delivery system including temperature-sensitive control of drug delivery and/or the drug delivery system.

BACKGROUND

Patients commonly receive drugs to treat a wide variety of medical conditions. While certain drugs may be administered via peroral, topical, transmucosal, or inhalation routes, other drugs are administered via injection or infusion. These injections or infusions may include intradermal, subcutaneous, intramuscular, intravenous, and intraperitoneal methods. Typically, injections or infusions involve the use of a hollow cannula or needle through which the drug passes from a container to the patient.

With regard to the subcutaneous and intramuscular injection routes, considerable attention has been devoted to providing a reproducible motion relative to the insertion of the cannula or needle through the skin to position the needle at a proper distance into the body, and then to provide a reproducible rate of delivery through the cannula or needle into the patient. Very often, providing a reproducible rate of delivery involves providing a reproducible motion for the movement of a plunger along the inside of a syringe or cartridge. Various mechanisms have been designed for controlled release of stored energy to advance the needle into the patient, and then to advance the plunger relative to the bore of the syringe or cartridge. Springs, motors, chemical reactions, and phase-changing materials have all been considered to provide the motive force for advancement of the needle and/or the plunger. Reproducible motion is considered fundamental to predictable drug delivery.

To the extent that a controller is included in such a drug delivery device, the controller controls the source of stored energy to ensure that it is released in a reproducible fashion. This may involve ensuring that various springs or motors are actuated such that one motion follows another in a predetermined sequence, thereby ensuring safe and effective delivery of the drug via the cannula or needle into the patient.

SUMMARY

According to an aspect of the present disclosure, a drug delivery system includes a reservoir adapted to contain a drug, and a drug delivery device coupled to the reservoir to deliver a drug from the reservoir. The drug delivery device also includes a lock having a locked state wherein delivery of the drug from the reservoir is limited and an unlocked state wherein delivery of the drug from the reservoir is not limited. The system further includes a temperature sensor, an output device, and a controller coupled to the lock, the temperature sensor, and the output device. The controller is programmed (a) to determine if the temperature of a drug disposed in the reservoir exceeds an upper limit, and if the temperature exceeds the upper limit, to activate the output device at least once and to place the lock in the locked state, (b) to determine if the temperature of a drug disposed in the reservoir is below a lower limit, and if the temperature is below the lower limit, to activate the output device at least once and to place the lock in the locked state, and (c) to determine if the temperature of the drug is between the upper limit and the lower limit subsequent to (b), and if the temperature is between the upper limit and the lower limit, to place the lock in the unlocked state.

According to another aspect of the present disclosure, a drug delivery system includes a reservoir adapted to contain a drug, and a drug delivery device coupled to the reservoir to deliver a drug from the reservoir. The drug delivery device also includes at least one temperature-sensitive component and a lock having a locked state wherein delivery of the drug from the reservoir is limited and an unlocked state wherein delivery of the drug from the reservoir is not limited. The system further includes a temperature sensor, an output device, and a controller coupled to the lock, the temperature sensor, and the output device. The controller is programmed (a) to determine if the temperature of the at least one temperature-sensitive component exceeds an upper limit, and if the temperature exceeds the upper limit, to activate the output device at least once and to place the lock in the locked state, (b) to determine if the temperature of the at least one temperature-sensitive component is below a lower limit, and if the temperature is below the lower limit, to activate the output device at least once and to place the lock in the locked state, and (c) to determine if the temperature of the at least one temperature-sensitive component is between the upper limit and the lower limit subsequent to (b), and if the temperature is between the upper limit and the lower limit, to place the lock in the unlocked state.

According to a further aspect of the present disclosure, a drug delivery system includes a reservoir adapted to contain a drug, and a drug delivery device coupled to the reservoir to deliver a drug from the reservoir. The drug delivery device also includes a lock having a locked state wherein delivery of the drug from the reservoir is limited and an unlocked state wherein delivery of the drug from the reservoir is not limited. The system further includes a temperature sensor, an output device, and a controller coupled to the lock, the temperature sensor, and the output device. The controller is programmed (a) to determine if the temperature of a drug disposed in the reservoir exceeds an upper limit, and if the temperature exceeds the upper limit, to activate the output device at least once and to place the lock in the locked state, (b) to determine if temperature of a drug disposed in the reservoir is below a lower limit, and if the temperature is below the lower limit, to activate the output device at least once and to place the lock in the locked state, and (c) to determine if a time period has elapsed subsequent to (b), and if the time period has elapsed, to place the lock in the unlocked state.

According to a still further aspect of the present disclosure, a drug delivery system includes a reservoir adapted to contain a drug, and a drug delivery device coupled to the reservoir to deliver a drug from the reservoir. The drug delivery device also includes a lock having a locked state wherein delivery of the drug from the reservoir is limited and an unlocked state wherein delivery of the drug from the reservoir is not limited. The system further includes an output device, and a controller coupled to the lock and the output device. The controller includes a temperature sensor, and is configured to (a) to determine if the temperature of a drug disposed in the reservoir is below a lower limit, and if the temperature is below the lower limit, to activate the output device at least once and to place the lock in the locked state, and (b) to determine if the temperature of the drug is between the upper limit and the lower limit subsequent to (a), and if the temperature is between the upper limit and the lower limit, to place the lock in the unlocked state. In addition or in the alternative, this controller may be configured to determine if the drug is above an upper limit, and if so, take appropriate action.

According to yet another aspect of the present disclosure, a method of delivering a drug product includes determining if the temperature of a drug disposed in a reservoir of a drug delivery system is below a lower limit, and if the temperature is below the lower limit, to activate an output device at least once; and providing instructions to a user of the drug delivery system that if the output device is activated, to operate the drug delivery system only after a period of time has elapsed after the output device has been activated.

BRIEF DESCRIPTION OF THE DRAWINGS

The disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 8 is a perspective view of a drug delivery system according to an embodiment of the present disclosure, with an associated syringe which may be used to fill the device;

FIG. 9 is a cross-sectional view of the drug delivery device of FIG. 8 taken along line 9-9;

FIG. 10 is a cross-sectional view of the drug delivery device of FIG. 9 taken along line 10-10;

DETAILED DESCRIPTION OF VARIOUS EMBODIMENTS

Figure 1:
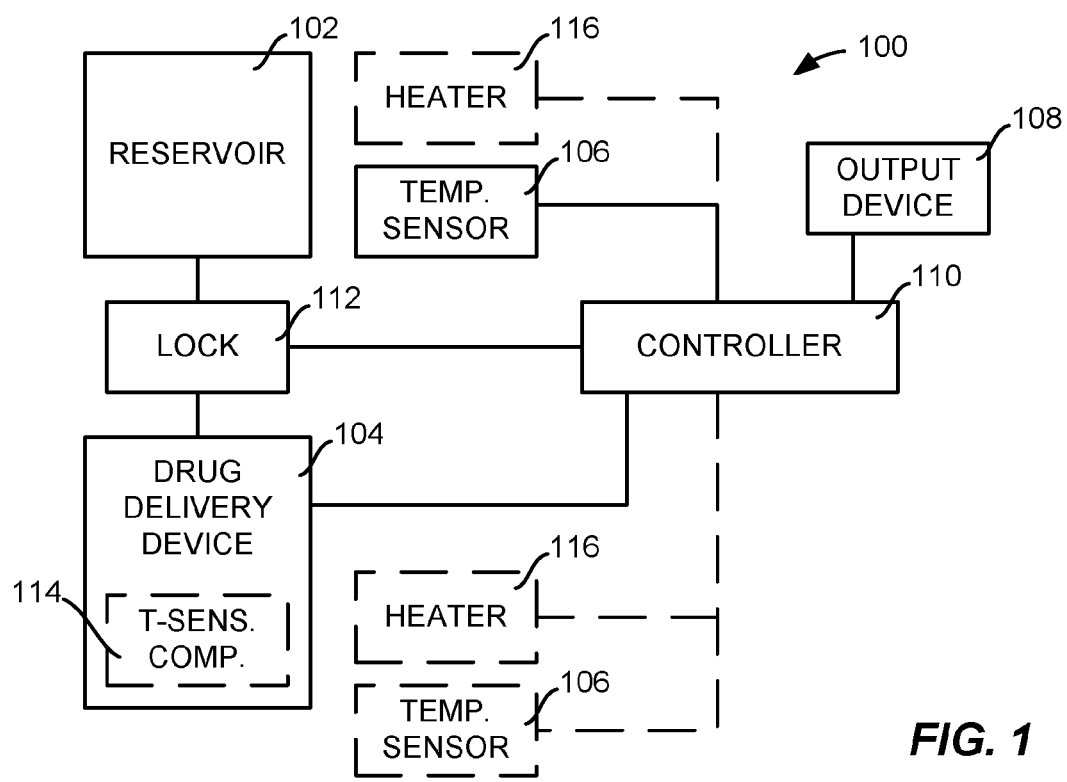
FIG. 1 is a schematic view of a drug delivery system according to one embodiment of the disclosure.

A drug may be injected or infused using a variety of different approaches, technologies, and systems. For example, the drug may be filled into a reservoir in the form of a syringe, and then the syringe may be used to administer (inject) the drug subcutaneously. Alternatively, the drug may be filled into a reservoir in the form of a syringe or other appropriate primary container, e.g., a cartridge, and then the pre-filled syringe or other container may be combined with an autoinjector that may be used to automate the movement of a plunger within the bore of the syringe or container, and optionally the insertion of a cannula or needle into the patient. For example, the autoinjector may include a drive (e.g., a motor, spring(s), propellant reservoir, etc.) that causes the container to move within a housing and/or the plunger to move within the container upon manipulation of an actuator (e.g., depressing a button). As a still further alternative, the drug may be filled into a reservoir (or container), and the reservoir may be manipulated with a pump or drive (which may take the form of a motor, spring(s), propellant reservoir, etc.) that infuses the drug through a needle, cannula or catheter into the patient. The pump and the reservoir may be disposed within a housing, which housing may be attached to the patient to form an on-body drug delivery system, for example.

In whatever form the drug delivery system may take, it remains important to follow the appropriate storage recommendations for the drug to be injected or infused, because failure to follow these recommendations can result in sub-potent or incomplete delivery of pharmaceutical products, and potentially therapeutic failure. For example, the storage recommendations for certain products require storage at low temperatures (2-8° C.), i.e., refrigeration. If the pharmaceutical product is exposed to temperatures outside the recommended range, the product may become compromised and it may be necessary to discard the product. Exposure to temperatures outside the recommended range may occur naturally with exposure to environmental conditions.

Given the variety of different approaches, technologies, and systems for drug delivery, there are a number of different options for storage of the drug and the associated drug delivery device. For example, the drug may be refrigerated in its (primary) container or reservoir (e.g., pre-filled syringe, cartridge, etc.), while the associated drug delivery device (e.g., autoinjector, on-body drug delivery system) may be stored at room temperature, the reservoir being combined with the remainder of the drug delivery device at the time of use. Alternatively, the drug (positioned in its container or reservoir) and the associated drug delivery device may be refrigerated together. For example, the reservoir may be combined with the associated drug delivery device prior to or during refrigeration, such that the device is already assembled for use upon removal from storage. It is also possible that the drug-filled container and the drug delivery device may be disposed in the same packaging for storage (e.g., as a kit), but the drug-filled reservoir has not been disposed within the drug delivery device.

Storage of certain drug products (with or without the associated drug delivery device) at low temperatures may be important to prevent a subpotent product or incomplete or suboptimal delivery. For example, storage at low temperature may affect the physical characteristics of drug product or the action of the drug delivery device. Certain drug products exhibit increased viscosity at lower temperatures, which may inhibit delivery or make the rate of delivery less predictable soon after removal from the low temperature. Other drug products may become more viscous with increased temperature and therefore more difficult or less predictable to deliver the longer the drug is kept at room temperature. In addition, if the drug device is refrigerated with the drug, the storage at low temperatures may affect the performance of the drug delivery device. For example, the electrical discharge of batteries is known to change with temperature, providing less energy at reduced temperature, which may make delivery more difficult or less predictable soon after the device is removed from refrigeration where the drive relies upon an on-board battery. Further, storage at low temperatures may affect patient comfort when the drug is delivered. Certain patients will find administration of low temperature fluids to be painful. In addition, reductions in the rate of injection/infusion caused by low temperature effects on the drug and/or the device may be considered to be painful.

Once the drug product (and optionally the drug delivery device) is removed from storage, exposure to high temperatures may result in suboptimal drug delivery or delivery of a subpotent drug product. As noted above, depending on the storage recommendations, exposure to too high temperatures may require disposal of the drug product. Exposure to too high temperatures may also affect components of the drug delivery device, such as the battery.

This disclosure focuses on a drug delivery system that is sensitive to the temperature changes that the drug and/or device may undergo, and considers these temperature changes in controlling the delivery of the drug and/or operation of the drug delivery device. As a consequence, the drug delivery system according to the present disclosure may alter its operation based on the temperature of the drug and/or the device to ensure that the delivery of the drug is safe, comfortable, and predictable over a wide range of environmental and operating conditions.

FIG. 1 is a schematic of a drug delivery system 100 according to one embodiment of the disclosure. The drug delivery system 100 includes a number of components or subassemblies, such as a reservoir 102, a drug delivery device 104, a temperature sensor 106, an output device 108, and a controller 110. The details of each of these components or subassemblies will be discussed below relative to a series of non-limiting examples.

The reservoir 102 is adapted to contain a drug. The drug delivery device 104 is coupled to the reservoir 102 to deliver the drug from the reservoir 102. The drug delivery system 100 includes a lock 112 having a locked state wherein delivery of the drug from the reservoir 102 is limited and an unlocked state wherein delivery of the drug from the reservoir 102 is not limited. According to certain embodiments, the lock 112 may substantially prevent delivery of the drug from the reservoir 102 by disposing or maintaining a physical barrier between the drug delivery device 104 and the reservoir 102, or by preventing the operation of the drug delivery device 104. According to some embodiments, the substantial prevention of the delivery of the drug from the reservoir 102 may mean that flow of the drug from the reservoir 102 through the drug delivery device 104 is less than about 15%, 10%, 5% or 1% of the flow of the drug from the reservoir 102 through the drug delivery device 104 in the unlocked state. In addition, in some embodiments, the lock 112 in the unlocked state may move or remove the physical barrier between the drug delivery device 104 and the reservoir 102, or may permit the drug delivery device 104 to operate. According to certain embodiments, permitting the delivery of the drug from the reservoir 102 may mean that flow of the drug from the reservoir 102 through the drug delivery device 104 is at least about 85%, 90%, 95% or 99% of the maximum flow possible of the drug from the reservoir 102 through the drug delivery device 104.

In some embodiments, the controller 110 is coupled to the lock 112, the temperature sensor 106, and the output device 108. The controller 110 may include a processor and memory, which processor may be programmed to receive a signal or signals from the temperature sensor 106 and control (e.g., activate) the output device 108 and the lock 112. Alternatively, the controller 110 may be a mechanical device or assembly that integrates functions of the temperature sensor 106 and the lock 112 while controlling or actuating the output device 108. For example, the controller 110 may include a strip of shape memory metal that assumes a particular shape when the metal is above or below a particular temperature threshold, the strip being secured relative to a fluid flow path (e.g., tubing) that connects the reservoir 102 to the drug delivery device 104 such that when the strip assumes the afore-mentioned shape, the strip impinges on the fluid flow path so as to open or close the fluid flow path. The strip may thus function as the temperature sensor 106 and the lock 112, as well as being part of the controller 110. It will also be recognized that the controller may include mechanical and electrical components or subassemblies, as well as chemical or biologic components or subassemblies.

Figure 2:
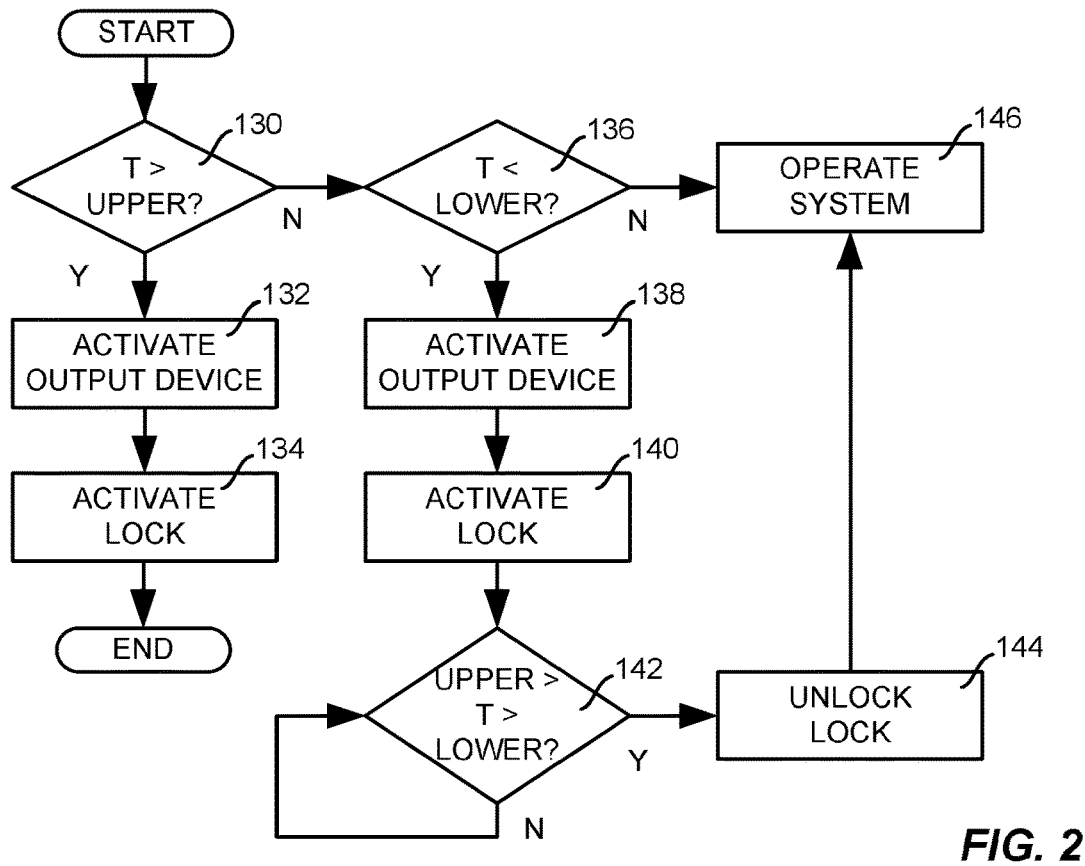
FIG. 2 is a block diagram of the operation of a drug delivery system such as illustrated in FIG. 1 according to an embodiment addressing high and low temperature conditions of the drug and controlling delivery directly according to temperature.

According to some embodiments and as illustrated in FIGS. 1 and 2, the controller 110 may be configured to determine (e.g., in the case of an electrical embodiment, be programmed to determine) if the temperature of the drug disposed in the reservoir 102 exceeds an upper limit at block 130. According to some embodiments, the determination may be based on a signal received by the controller 110 from the temperature sensor 106. If the temperature exceeds the upper limit at block 130, the controller 110 may activate the output device 108 at least once at block 132 (e.g., to alert the user that the temperature of the drug is too high for safety) and place the lock 112 in the locked state at block 134. If the temperature is below the upper limit at block 130, the controller 110 may determine (or may be programmed to determine) if the temperature of the drug disposed in the reservoir 102 is below a lower limit at block 136, and if the temperature is below the lower limit, may activate the output device 108 at least once at block 138 (e.g., to alert the user that the temperature of the drug is too low for safety, for comfortable delivery and/or for predictable delivery) and place the lock 112 in the locked state at block 140. Further, the controller 110 may determine (or may be programmed to determine) at block 142 if the temperature of the drug is between the upper limit and the lower limit subsequent to block 136 (and blocks 138, 140), and if the temperature is between the upper limit and the lower limit, to place the lock 112 in the unlocked state at block 144 thus permitting operation at block 146. This last step may be combined with activation of the output device 108 to alert the user that the device is within acceptable range for delivery.

Figure 3:
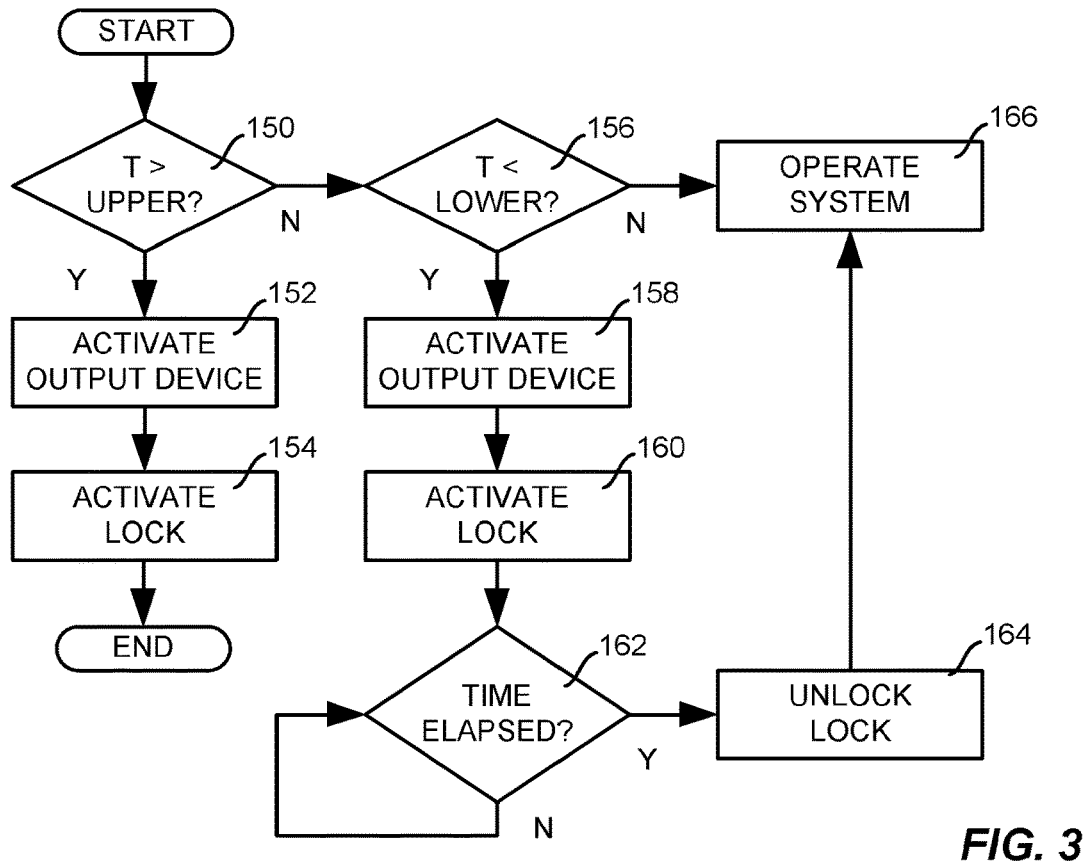
FIG. 3 is a block diagram of the operation of a drug delivery system such as illustrated in FIG. 1 according to an embodiment addressing high and low temperature conditions of the drug and controlling delivery directly according to a lapse of time, and indirectly according to temperature.

According to other embodiments and as illustrated in FIGS. 1 and 3, the controller 110 may determine if the temperature of the drug disposed in the reservoir 102 exceeds an upper limit (for example, by receiving a signal from the temperature sensor 106) at block 150, and if the temperature exceeds the upper limit, may activate the output device 108 at least once at block 152 and place the lock 112 in the locked state at block 154. The controller 110 may also be programmed to determine if the temperature of a drug disposed in the reservoir 102 is below a lower limit (by receiving a signal from the temperature sensor 106) at block 156, and if the temperature is below the lower limit, may activate the output device 108 at least once at block 158 and place the lock 112 in the locked state at block 160. Further, the controller 110 may determine at block 162 if a time period has elapsed subsequent to block 156 (and blocks 158, 160), and if the time period has elapsed, may place the lock 112 in the unlocked state at block 164 thus permitting operation at block 166. In some embodiments, where the controller 110 includes a processor, the controller 110 may be programmed to carry out the afore-mentioned determinations and activations of FIG. 3, or the controller 110 may be configured to perform those actions.

Figure 4:
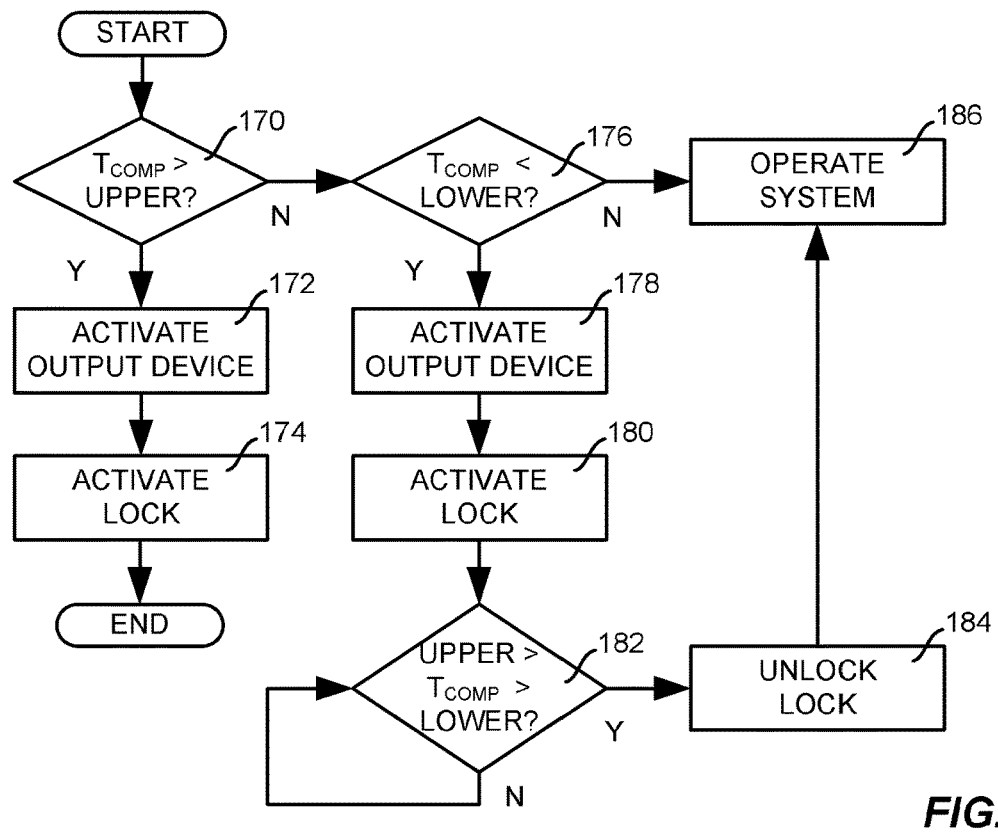
FIG. 4 is a block diagram of the operation of a drug delivery system such as illustrated in FIG. 1 according to an embodiment addressing high and low temperature conditions of the drug delivery device and controlling delivery according to temperature.

According to other embodiments and as illustrated in FIGS. 1 and 4, the drug delivery device 104 may optionally include at least one temperature-sensitive component ("T-Sens. Comp.") 114 and the lock 112 having a locked state wherein delivery of the drug from the reservoir 102 is limited and an unlocked state wherein delivery of the drug from the reservoir 102 is not limited. According to such an embodiment, the controller 110 would be coupled to the lock 112, an optional (or additional) temperature sensor 106, and the output device 108, and would determine if the temperature of the at least one temperature-sensitive component 114 exceeds an upper limit at block 170, and if the temperature exceeds the upper limit, may activate the output device 108 at least once at block 172 and place the lock 112 in the locked state at block 174. The controller 110 may also determine if the temperature of the at least one temperature-sensitive component 114 is below a lower limit at block 176, and if the temperature is below the lower limit, may activate the output device 108 at least once at block 178 and place the lock 112 in the locked state at block 180. The controller 110 may be configured to determine at block 182 if the temperature of the at least one temperature-sensitive component 114 is between the upper limit and the lower limit subsequent to block 176, and if the temperature is between the upper limit and the lower limit, place the lock 112 in the unlocked state at block 184 permitting operation at block 186. Again, where the controller 110 includes a processor, the controller 110 may be programmed to carry out the afore-mentioned determinations and activations, or the controller 110 may be otherwise configured to perform those actions. According to such an embodiment, at least one temperature-sensitive component 114 may be a battery.

Further refinements may be included in any of the foregoing embodiments.

Figure 5:
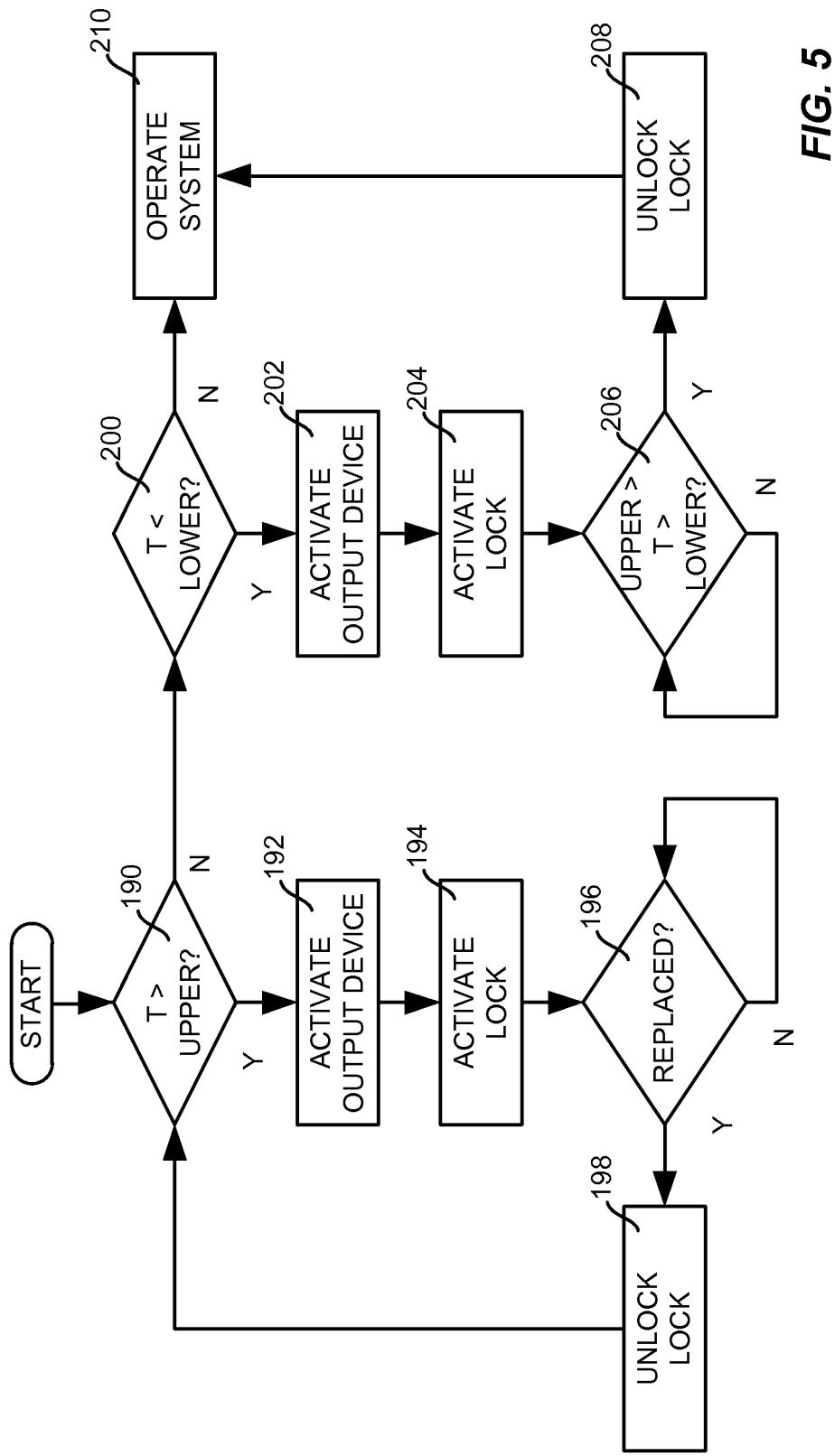
FIG. 5 is a block diagram of the operation of a drug delivery system such as illustrated in FIG. 1 according an embodiment addressing high temperature conditions of the drug with removal/replacement.

For example, the reservoir 102 may adapted to be removed from the drug delivery system 100. According to such embodiments and as illustrated in FIGS. 1 and 5, the controller 110 is configured or programmed to determine if the temperature of the drug in the reservoir 102 exceeds a particular temperature at block 190. After determining that the temperature exceeds a threshold temperature at block 190 (and after activating the output device at block 192 and the lock at block 194), the controller 110 may determine (or may be programmed to determine) at block 196 if the reservoir 102 has been removed and replaced with another reservoir 102 adapted to contain a drug subsequent to block 190. If the reservoir 102 has been removed and replaced with another reservoir 102, the controller 110 may place the lock 112 in the unlocked state at block 198. The device may then again determine if the temperature of the drug disposed in the reservoir 102 is above the upper limit at block 190 and, if it is not, the device may then determine is the temperature of the drug disposed in the reservoir 102 is below a lower limit at block 200. If the temperature of the drug in the reservoir 102 is below the lower limit, the device may activate the output device 108 at least once at block 202 and place the lock 112 in the locked state at block 204. Further, the controller 110 may determine (or may be programmed to determine) at block 206 if the temperature of the drug is between the upper limit and the lower limit subsequent to block 200 (and blocks 202, 204), and if the temperature is between the upper limit and the lower limit, to place the lock 112 in the unlocked state at block 208 thus permitting operation at block 210. It will be recognized that such a method may also be adapted to permit the determination of a high temperature condition of a temperature-sensitive component 114 of the drug delivery system (e.g., a battery), and the monitoring of the replacement of the battery and subsequent operation of the system 200.

Figure 6:
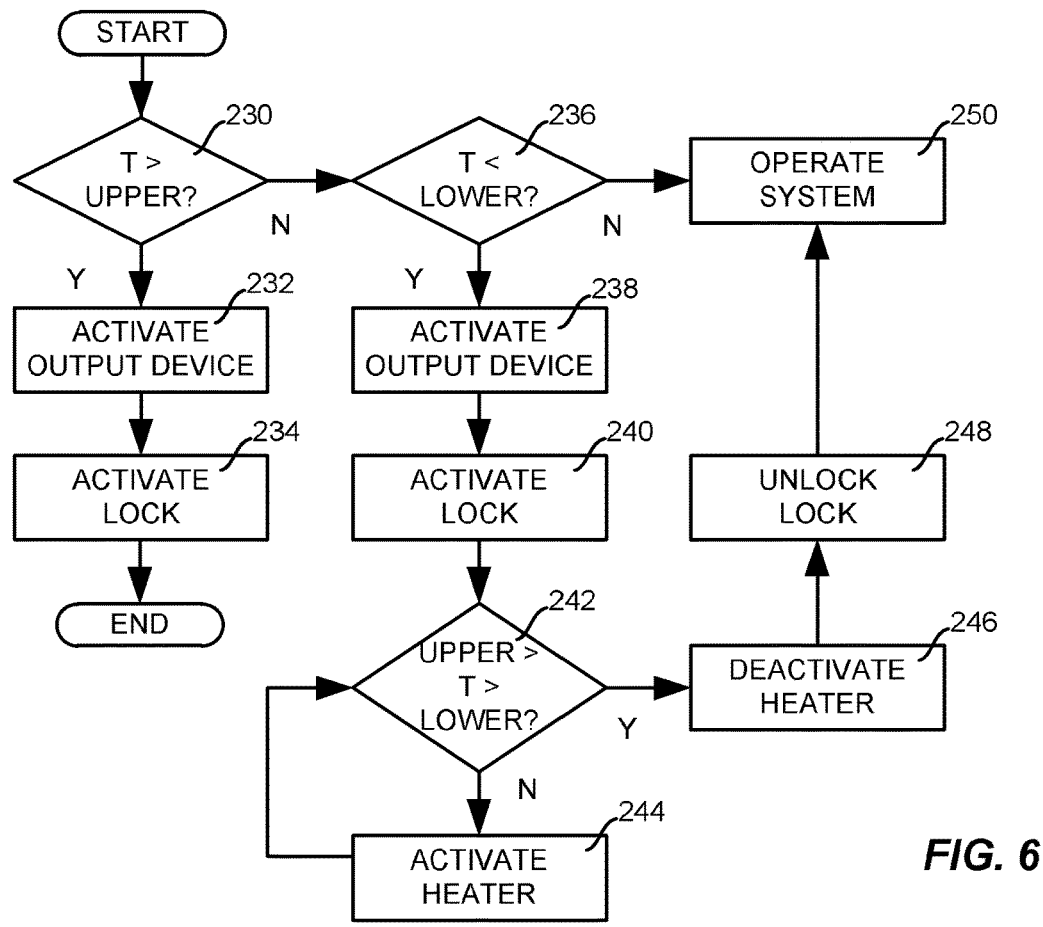
FIG. 6 is a block diagram of the operation of a drug delivery system such as illustrated in FIG. 1 according to an embodiment addressing low temperature conditions of the drug through incorporation of a heater.

According to other embodiments, the drug delivery system 100 may include a heater 116 coupled to the controller 110 and proximate to at least one of the reservoir 102 and the drug delivery device 104 (see FIG. 1). As illustrated in FIGS. 1 and 6, the controller 110 may determine (or in the case of an electrical embodiment, may be programmed to determine) if the temperature of a drug disposed in the reservoir 102, for example, exceeds an upper limit at block 230. If the temperature exceeds the upper limit, the controller 110 may activate the output device 108 at least once at block 232 and place the lock 112 in the locked state at block 234. If the temperature is below the upper limit, the controller 110 may determine (or may be programmed to determine) if the temperature of a drug disposed in the reservoir 102 is below a lower limit at block 236, and if the temperature is below the lower limit, may activate the output device 108 at least once at block 238 and place the lock 112 in the locked state at block 240. Further, the controller 110 may determine (or may be programmed to determine) at block 242 if the temperature of the drug is between the upper limit and the lower limit subsequent to block 236 (and blocks 238, 240), and the controller 110 may be programmed to activate the heater 116 at block 244 if the temperature of the drug is below the lower limit, and to deactivate the heater 116 at block 246 if the temperature of the drug is between the upper and lower limits. After or contemporaneous with deactivating the heater 116 at block 246, the controller 110 may unlock the lock 112 at block 248 permitting operation at block 250.

Figure 7:
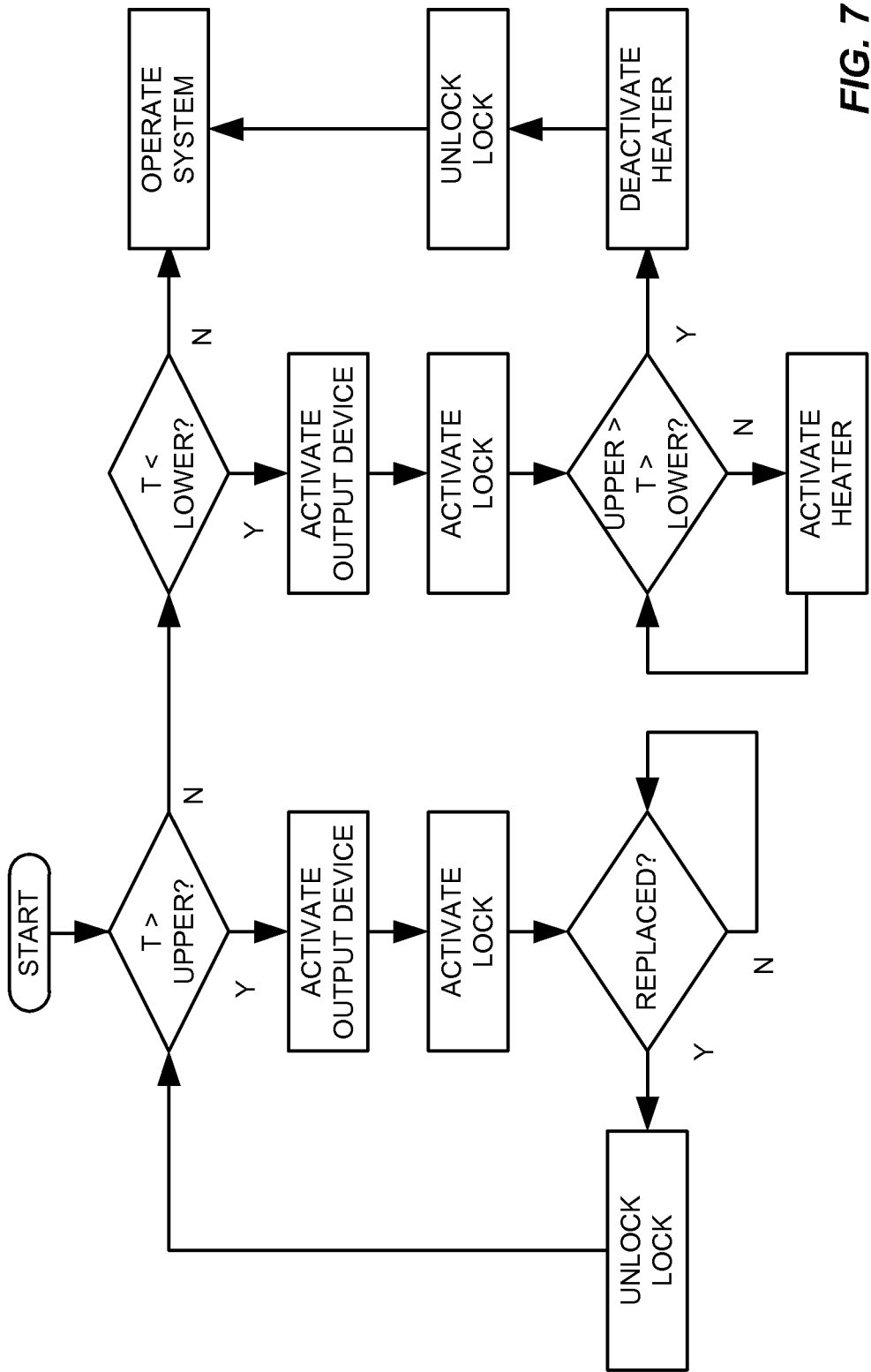
FIG. 7 is a block diagram of the operation of a drug delivery system such as illustrated in FIG. 1 according an embodiment addressing high temperature conditions of the drug with removal/replacement and addressing low temperature conditions as to the drug through incorporation of a heater.

It will be recognized that the methods of operation of the system 100 described in FIGS. 2-6 may be combined with each other. For example, the system may perform both the method according to FIG. 2 or FIG. 3 in combination with that of FIG. 4. Similarly, FIG. 4 may be performed with reference to the lapse of a particular time period at block 182 (as illustrated in FIG. 3 relative to the reservoir) instead of with reference to a particular temperature range. Further, the steps in blocks 156-164 in FIG. 3 may be substituted for those in blocks 200-208 in FIG. 5. In addition, the steps of activating and deactivating a heater illustrated in blocks 244, 246 of FIG. 6 may be combined with any of the methods of operation illustrated in FIGS. 2-5, as would be recognized from the foregoing description (see, e.g., FIG. 7 as compared to FIG. 5).

Having described the structure and operation of the drug delivery system in general terms (see FIGS. 1-7), further exemplary details are provided regarding the reservoir, drug delivery device, temperature sensor, output device, controller, lock, and heater. In particular, an embodiment of a drug delivery system 300 incorporating the features of FIG. 1 and adding further details is illustrated in FIGS. 8-10.

FIG. 8 illustrates a drug delivery system 300. The system 300 may be a wearable, disposable system. The system 300 may include a disposable housing 302 that may be attached to a patient or wearer with adhesive, for example.

The disposable housing 302 may be made of a plastic material. As seen in FIG. 9, the housing 302 may be defined by two sections, a plate 304 that is applied against the wearer's skin, and a dome 306 that is attached to the plate 304, preferably by a seal at an interface between a peripheral edge 308 of the plate 304 and a peripheral edge 310 of the dome 306.

As shown in FIG. 9, the housing 302 has an interior surface 312 defining an interior space 314, and an exterior surface 316. In particular, the plate 304 has an interior surface 318 and an exterior surface 320, and the dome 306 has an interior surface 322 and an exterior surface 324. According to the illustrated embodiment, the interior surface 312 of the housing 302 is defined by the interior surfaces 318, 322 of the plate 304 and the dome 306, while the exterior surface 316 of the housing 302 is defined by the exterior surfaces 320, 324 of the plate 304 and dome 306.

As noted above, the housing 302 may be attached to the skin of the wearer. In some embodiments, an adhesive may be used. The adhesive may be adapted to releasably secure the housing to skin during a single application. As shown in FIG. 9, the adhesive is disposed in a layer 326 on a portion 328 of the exterior surface 316 of the housing 302, and in particular on the exterior surface 320 of the plate 304. The adhesive is covered with a removable, disposable sheet 330 prior to application of the housing 302 to the skin of the wearer.

As seen in FIGS. 9 and 10, a reservoir 340, a drive 342, a needle 344, and an injector 346 are disposed in the housing 302. With reference to the embodiment illustrated in FIG. 1, the reservoir 340 may correspond to the reservoir 102, while the drive 342, needle 344, and the injector 346 may correspond to the drug delivery device 104. It will be recognized that additional components and subassemblies may be provided that would also be considered to correspond to the drug delivery device 104.

In some embodiments, the reservoir 340 may be defined at least in part by a combination of a rigid-walled cylinder or bore 360 having a port 362 at a first end 364 and a plunger 366 fitted to move along a longitudinal axis 368 of the cylinder 360 between a second end 370 and the first end 364 to force drug out of the reservoir 340 through the port 362 (FIG. 9). The movement of the plunger 366 may be caused by the operation of the drive 342.

Figure 11:
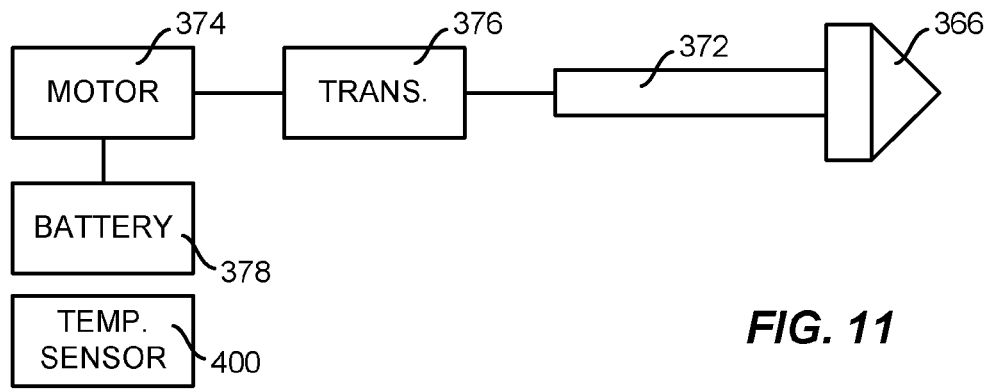
FIG. 11 is a schematic view of a drive for use in the drug delivery system according to FIG. 8.

The drive 342 may be similar in structure and operation to the mechanisms for moving a plunger along a cylinder as may be found in U.S. Pat. Nos. 6,656,158; 6,656,159; 7,128,727; and 7,144,384, which patents are incorporated by reference herein for all purposes. As illustrated in FIG. 11, the drive 342 may include a plunger arm 372, a motor 374, a transmission 376 and a battery 378. The plunger arm 372 is in contact at least at a first end with the plunger 366 to urge the plunger 366 along the cylinder 360, and the transmission 376 is coupled to the plunger arm 366 and the motor 374 to cause the plunger arm 372 to move according to the operation of the motor 374. The battery 378 provides a source of electrical power for the motor 374. The combination of the motor 374, transmission 376 and battery 378 may also be referred to as one example of an actuator.

According to other embodiments, a non-rigid collapsible pouch may be substituted for the rigid-walled cylinder 360 and the plunger 366 shown in FIG. 9. It will be recognized that where the reservoir 360 is in the form of a non-rigid collapsible pouch, a spring-based mechanical system may be used to compress and pressurize the reservoir. According to still further variants, a non-mechanical system may be used to move the plunger 366 or compress the bag. For example, a gas-generating system may be used, including a two-component system wherein the components are kept apart until the gas is to be generated, in which case they are combined. In other embodiments, a swellable gel may be used, wherein the introduction of water from a source internal to the device causes the gel to increase in dimension to move the plunger or compress the pouch. As a further example, a propellant reservoir may be opened and the propellant discharged to move the plunger 366 or compress the bag. Examples of such mechanisms may be found in U.S. Pat. Nos. 5,957,895; 5,858,001; and 5,814,020, which patents are incorporated by reference herein for all purposes.

According to certain embodiments, the reservoir 340 may be a pre-filled container, such as a pre-filled cartridge or a pre-filled syringe. Alternatively, the delivery system 300 may include a fill port 380 in fluid communication with the reservoir 340, the fill port 380 adapted to receive a luer tip of a syringe (e.g., syringe illustrated in FIG. 8), although a rubber septum may be used instead, for example. In use, a healthcare provider may inject the drug from the syringe through the fill port 380 into the reservoir 340, and the syringe may be provided as a pre-filled syringe (filled with any of the materials mentioned herein) to the healthcare provider with the delivery system 300 as a kit.

The needle 344 may have a retracted state wherein a pointed end 390 (in fact, the entire needle 344) may be withdrawn inside the housing 302 and a deployed state wherein the pointed end 390 projects from the housing 302 (see FIGS. 12 and 13), the injector 346 moving the needle 344 from the retracted state to the deployed state. Examples of exemplary injectors may be found in U.S. Pat. Nos. 7,128,727 and 7,144,384, which patents are incorporated by reference herein for all purposes.

The needle 344 may be hollow, and may be used to administer the drug directly to the patient. Alternatively, the needle 344 may be used in conjunction with a cannula or catheter 392, the needle 344 being used to insert the catheter 392 into the patient through the injection site, and the drug passing through the catheter 392 into the patient during administration (see FIGS. 9 and 10). Phrased slightly differently, the system 300 may, according to certain exemplary embodiments, automatically insert a soft cannula into the subcutaneous tissue.

Figure 12:
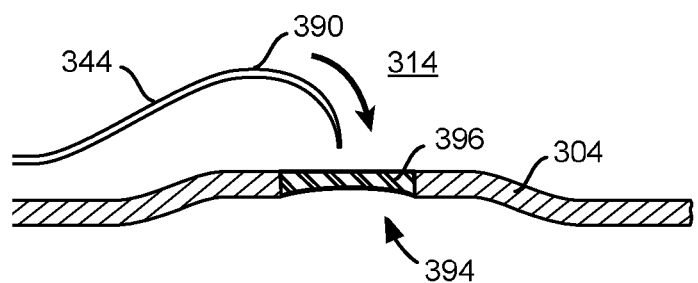
FIG. 12 is an enlarged, fragmentary, cross-sectional view of a barrier system used in conjunction with a needle according to the disclosure, with the needle in a retracted state.
Figure 13:
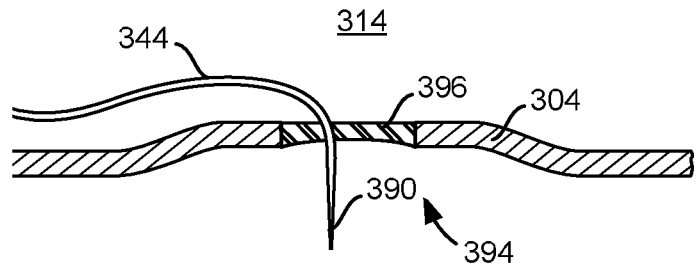
FIG. 13 is an enlarged, fragmentary, cross-sectional view of the barrier system of FIG. 12, with the needle in a deployed state.

As illustrated in FIGS. 9, 12, and 13, the housing 302 (specifically the plate 304) may have an aperture or opening 394 formed therein to permit the needle 344 (and catheter 392) to pass therethrough. According to certain embodiments, the aperture 394 may be unobstructed, such that there is no impediment or obstacle to the movement of the needle 344 (and catheter 392) through the opening 394. However, to better maintain the sterility of the needle 344 and the device's container closure integrity (CCI), a septum 396 (shown in FIGS. 12 and 13) may be disposed in or over the aperture 394.

The septum 396, which may be made of a rubber, is disposed between the needle 344 (and the space 314) and the patient's skin with the needle 344 in the retracted state (FIG. 12). In the deployed state (FIG. 13), at least a portion of the needle 344 (i.e., the pointed end 390) will depend from the space 314 through the septum 396. As such, the septum 396 is always present as a barrier between the interior space 314 and the external environment.

The system 300 also includes at least one temperature sensor 400.

Figure 14:
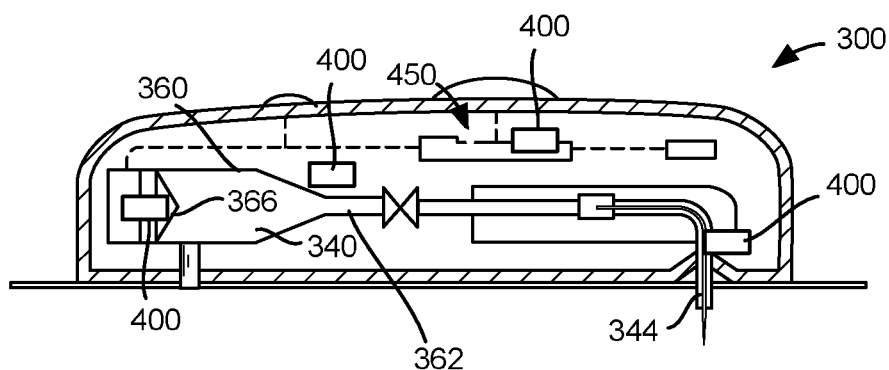
FIG. 14 is a cross-sectional view illustrating the placement of the temperature sensor.

As illustrated in FIG. 14, the at least one temperature sensor 400 may be disposed in different locations throughout the housing 302. For example, in embodiments where the reservoir 340 includes a cylinder 360 with a port 362 and a plunger 366 moveable within the cylinder 360 relative to the port 362 to force drug out of the port 362, the temperature sensor 400 may be attached to the plunger 366. In such a situation, the temperature sensor 400 may be in direct contact with the drug (e.g., disposed on an inner surface of the plunger 366 in direct contact with the drug) or may not be in direct contact with the drug (e.g., disposed or embedded within the plunger 366). Alternatively, a sensor 400 may be disposed near or in contact with the reservoir 340, for example disposed near or in contact with the wall of the reservoir 340, which may be particularly useful where the reservoir is removable from the remainder of the system 300. Further, a sensor may be disposed near or on-board a controller. A sensor 400 may also be disposed near or in contact with the battery 378 (see FIG. 11). Where the reservoir 340 includes a cannula or tubing in fluid communication with the reservoir 340, the temperature sensor 400 may be coupled to the cannula. As illustrated in FIG. 14, the temperature sensor 400 is coupled to a cannula in the form of a needle 344.

The temperature sensor 400 may take on a variety of forms. For example, the temperature sensor may be at least one of a resistance temperature detector, a thermocouple, an infrared thermopile, and an assembly comprising a thermally-sensitive label and an optical detector. While these sensors could be solid state devices, the sensors may also be of an RFID-type. An RFID sensor may have an advantage over a solid state device in that an RFID sensor may require neither power nor electrical contact with the device. A solid state device may be connected to a power source (e.g., battery) through a set of contacts.

Relative to the examples described above, certain processor chips routinely include a temperature sensor. While some heat may be generated in the processor during operation, this localized increase in temperature may be accounted for relative to the temperature determination using the on-board sensor. The on-board sensor thus may be used to infer the temperature of other components of the delivery device, or even the reservoir, based on their proximity to the sensor. If the heat generation is large enough to overly influence the determined temperature of a distant component, a calculation of heat transfer characteristics within the device and/or reservoir can be used to create a reference map of internal temperatures at various locations. Such a reference map could be stored by the controller for use in the determination of the temperature of components and/or the reservoir.

As to the embodiments relating to the temperature sensor attached to the plunger, even if the sensor is placed in indirect contact with the drug product (e.g., the sensor is embedded in the plunger), the sensor and the drug product will equilibrate to the same temperature, particularly during long periods of refrigerated storage. As the product warms, the temperature determined at the plunger should generally track the temperature of the drug in the reservoir. A high thermal conductivity material may be used as an intermediate between the drug in the reservoir and the sensor attached to the plunger to improve the tracking of the two temperatures. Rate information (e.g., rate of temperature change) may be used in addition to the temperature measurements to improve the accuracy and/or correlation to the drug product temperature.

As to the embodiments relating to a temperature sensor associated with or disposed proximate to the reservoir (or a temperature-sensitive component), the sensor may be an IR thermopile chip, for example. Such a sensor measures the IR signature of a thermal source, and does so without direct contact with the source. These IR thermopiles may operate in a wavelength range of 0.7 µm to 1000 µm, and may have a footprint of less than 2 mm by 2 mm. An exemplary thermopile chip is the TMP006 chip manufactured by Texas Instruments (Dallas, Tex.), which is optimized for low power consumption and requires a supply current of less than 200 µA. Because such a sensor typically provides a determination of the ambient temperature, the ambient temperature may be used to predict how long the drug (or temperature-sensitive component) will take to reach a temperature above the lower temperature threshold. This prediction may rely on the ambient temperature as well as the thermal mass and thermal transfer properties of the drug (or temperature-sensitive component), and the processor may be programmed to perform the calculation or a reference table may be stored in memory for the processor to access once the ambient temperature is determined.

Also in regard to embodiments relating to a temperature sensor associated with or disposed proximate to the reservoir (or a temperature-sensitive component), the sensor may be a thermally-sensitive label used in conjunction with (coupled to) an optical pickup or sensor. The thermally-sensitive label will change its appearance when a threshold temperature is reached. The label may take the form of a physical label, a wax, a lacquer-like paint, or a liquid crystal polymer film, for example. The optical pickup can be used to determine this change in appearance, which can then be correlated with the threshold temperature to make a temperature determination. The optical pickup may have a footprint of less than 2.5 mm by 2.5 mm, and may draw less than 20 µA when in active mode, 0.5 µA when in low-power non-active mode. An exemplary optical pickup or sensor if the MAX44005 sensor sold by Maxim Integrated (San Jose, Calif.). According to such an embodiment, the coupling between the label and the pickup is non-contact, thus preventing direct physical interaction between the label and the pickup.

As to the embodiments relating to the temperature sensor attached to the cannula or needle, such a sensor may be formed using thin film sensors (RTDs) or fine gauge wires (thermocouples). Use of such technologies would allow the sensor to be disposed in thermal contact with the needle, and indirect contact with the drug product, by integration into the needle component. As needle components are frequently constructed of materials with high thermal conductivity, a sensor disposed on the needle would improve tracking between the temperature of the needle and the temperature of the drug product passing through the needle. Moreover, with the sensor disposed on the cannula, it may be possible to monitor the body/tissue temperature of the patient at the injection site as well.

The system 300 also includes a controller 450 that is coupled to the drive 342 and the injector 346, the controller 212 operating the drive 342 to deliver a volume of the drug from the reservoir 340 and the injector 346 to move the needle 344 between the retracted and deployed states. As illustrated in FIG. 10, the controller is also coupled to the sensor 400, an output device 452, a lock 454 and a heater 456.

According to the embodiment illustrated in FIG. 10, the controller 450 may include a programmable microprocessor 470, memory 472, and a power supply 474. The power supply 474 may include one or more batteries. According to certain embodiments, the controller 450 may be programmed to determine if the temperature sensor 400 is accurate prior to determining if the temperature of a drug disposed in the reservoir 340 or the drug delivery device (e.g., drive 342, injector 346) is above the upper limit, below the lower limit, or between the upper and lower limits. The determination of accuracy may include a determination that the temperature sensor 400 is connected, or may include a comparison of a determination of the temperature using a signal from the temperature sensor 400 to a determination of the temperature using a signal from another temperature sensor. The controller 450 may also be programmed to adjust a determination of a temperature if the temperature sensor is not accurate, for example with reference to a table stored in memory or through the use of a correction factor.

The output device 452 may include at least one of a display, a light and a speaker. According to some embodiments, the output device 452 may include more than one of a display, a light and/or a speaker. The purpose of the output device 452 is to alert the user to a change in operational state of the system, and according to the embodiments described above, this may involve alerting the user to at least two different changes in operational state—one in case of high temperature and another in case of low temperature. Consequently, the output device 452 may include more than one display, light, and/or speaker to provide different alerts for the change in operational state caused by high temperature and the change in operational state caused by low temperature. A single output device 452 may be controlled by the controller 450 to operate differently (e.g., display a different color, or provide a different sound or tone) depending on whether a change in operational state based on a high temperature condition or on a low temperature condition occurs.

The heater 456 may be one of a variety of different types. For example, the heater 456 may be at least one of a mechanical heater (e.g., heat from shape memory actuator), an electrical heater, a chemical heater, and a selectable coupling to a heat source. In some embodiments, the electrical heater may include at least one of a resistive heater and a thermoelectric heater (i.e., a heater which provides IR heat generation). In some embodiments, the heat source may include at least one of the controller (e.g., waste heat from the processor circuit board) and a patient to which the drug delivery system is attached (in which case a thermally conductive adhesive may be used). Regardless of the heater used, the fluid path may be lengthened or widened proximate to the heater to improve the localized heating of the fluid between the reservoir and the injection/infusion site. Alternatively, the packaging may provide heating capability, or an adhesive liner may be used to provide the heat (e.g., pulling of adhesive liner activates acrylic adhesive to provide heat).

Relative to resistive heaters, such a heater may be constructed by running electrical power through a relatively resistant element, with the electrical energy being converted to heat energy. The heat may then conduct or convect from the source to an adjoining drug product or temperature-sensitive component. The waste heat from the processor circuit board may be generated by resistive heating in the conductor traces, for example.

Relative to a thermoelectric heater, such a heater uses the Peltier effect to create a heat flux between the junction to two dissimilar metals with the application of electrical energy. A thermoelectric heater may provide certain advantages, in that the same structure may be used for cooling as well as heating, if so desired. Additionally, there are no moving parts, which should provide greater simplicity and longer life.

Relative to chemical heaters, such a heater may include two or more chemicals that react to provide heat. For example, crystallization of a supersaturated solution of sodium acetate may be used, which reaction may be initiated by nucleation at time of use and may provide heat for between 20 minutes and 2 hours depending on the volume of reactants used.

Figure 15:
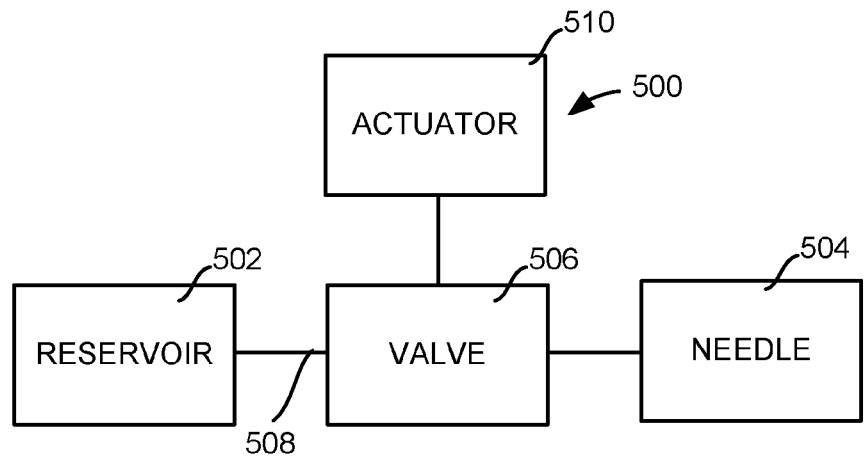
FIG. 15 is a schematic view of a mechanical controller according to the disclosure.

The controller 450 also may be a mechanical device, a combination of mechanical devices, a combination of electrical devices (hard-wired circuits or circuit components), or a combination of mechanical and electrical devices. FIG. 15 illustrates a particular embodiment of a mechanical controller 500 in combination with a reservoir 502, a needle 504, and a valve 506 disposed in a fluid flow path 508 between the reservoir 502 and the needle 504. The device including the controller 500, reservoir 502, needle 504, and valve 506 may include other devices (such as a drive for the reservoir 502 and/or an actuator for the needle 504), but these structures have been omitted for ease of explanation. The valve 506 may function as the lock in the embodiments described above, with the valve closed state corresponding to the locked state and the valve open state corresponding to the unlocked state.

The controller 500 includes an actuator 510 in the form of a temperature-sensitive material that may be used to change the lock state of the valve/lock 506, and which actuator 510 is disposed proximate to the drug and/or temperature-sensitive component that is to be monitored. The actuator 510 may include, for example, a strip of shape memory metal, such as nitanol (nickel titanium). Based on the temperature of the strip of shape memory metal, the strip may assume a first shape or a second shape. The temperature at which the strip changes between the first shape and the second shape may correspond to the lower temperature threshold. With the strip in the first shape, the strip may abut the valve 506 to place the valve 506 in its closed state. With the strip in the second shape, the strip may be spaced from the valve 506 so as to permit the valve 506 to assume its open state. Consequently, when the strip is at a temperature below the lower temperature threshold, the strip will ensure that the valve 506 is closed (locked), and when the strip is at a temperature above the lower temperature threshold, the strip will ensure that the valve 506 is open (unlocked).

In terms of the embodiments of methods illustrated in FIGS. 2 and 4, the controller 500 determines whether the temperature of the drug or a temperature-sensitive component is below a lower temperature threshold based on the shape of the strip of shape memory alloy. If the temperature of the strip is below the temperature at which the strip changes shape, then the strip will actuate the valve 506, corresponding to activation of the lock. The controller 500 determines if the temperature of the drug or the temperature-sensitive component is above the lower temperature threshold if the strip changes from the first shape to the second shape. If this occurs, the controller 500 unlocks the lock by virtue of the strip being spaced from the valve 506, permitting the valve to move to its open state, at which point drug may flow from the reservoir 402 to the needle 504.

Figure 16:
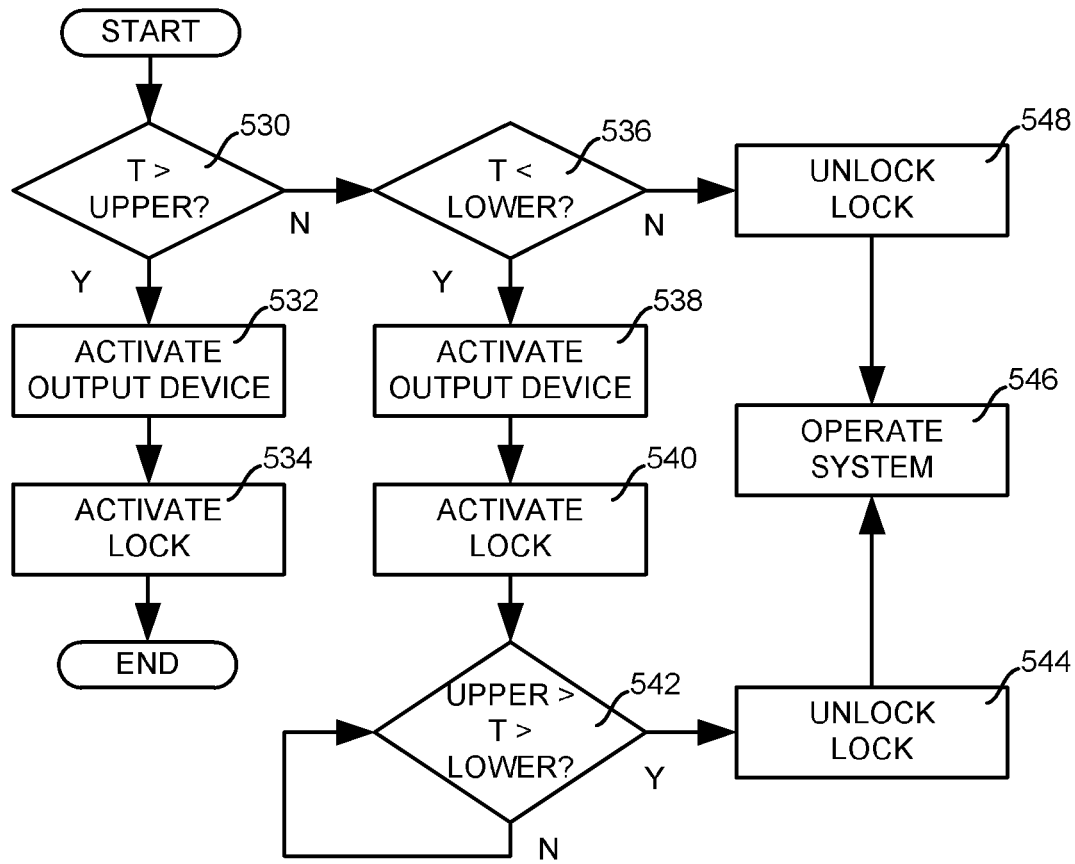
FIG. 16 is a block diagram of the operation of a drug delivery system such as illustrated in FIG. 1 according to an embodiment addressing high and low temperature conditions of the drug and controlling delivery directly according to temperature.

According to various embodiments, activation of the lock does not require the lock to have been in the unlocked state prior to its activation. The activation of the lock in some embodiments may also include or encompass permitting the lock to remain in its default locked state. As illustrated in FIG. 16, a controller may determine (or in the case of an electrical embodiment, may be programmed to determine) if the temperature of a drug disposed in a reservoir exceeds an upper limit at block 530. If the temperature exceeds the upper limit, the controller may activate an output device at least once at block 532 (e.g., to alert the user that the temperature of the drug is too high for safety) and place the lock in the locked state at block 534. In some embodiments, placing the lock in the locked state at block 534 includes the controller doing nothing at all because the lock is in the locked state by default. If the temperature is below the upper limit, the controller may determine (or may be programmed to determine) if the temperature of a drug disposed in the reservoir is below a lower limit at block 536, and if the temperature is below the lower limit, may activate the output device at least once at block 538 (e.g., to alert the user that the temperature of the drug is too low for safety, for comfortable delivery and/or for predictable delivery) and place the lock in the locked state at block 540. Similar to that described above, in some embodiments, placing the lock in the locked state at block 540 includes the controller doing nothing at all because the lock is in the locked state by default. Further, the controller may determine (or may be programmed to determine) at block 542 if the temperature of the drug is between the upper limit and the lower limit subsequent to block 536 (and blocks 538, 540). If the temperature is between the upper limit and the lower limit, the controller places the lock in the unlocked state at block 544 thus permitting operation at block 546. In embodiments where the lock is by default in the locked state, it will also be necessary for the controller to place the lock in the unlocked state at block 548.

The steps of the method according to FIG. 16 may be expressed in the same manner as those of the method according to FIG. 2, for example, except for the fact that the controller must also perform the step of unlocking the lock if it is determined that the temperature of the drug or the temperature-sensitive component is neither above the upper temperature threshold nor below the lower temperature threshold. Step 548 may thus be incorporated into any of the methods illustrated in FIGS. 2-7 to similar effect in an embodiment where the lock is locked by default.

Figure 17:
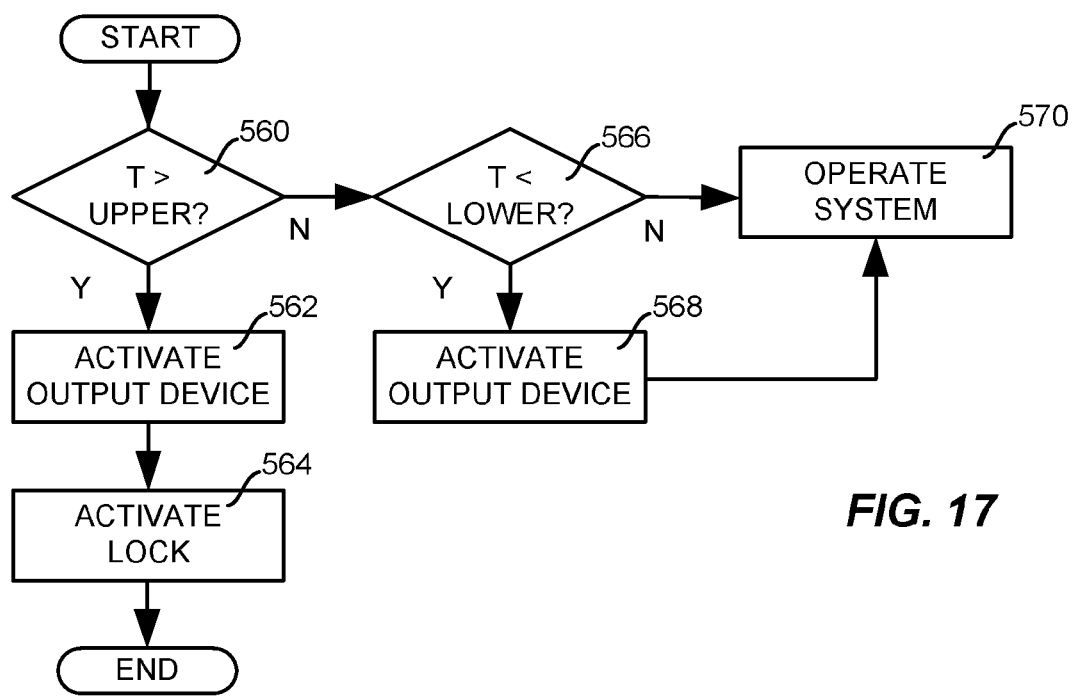
FIG. 17 is a block diagram of the operation of a drug delivery system such as illustrated in FIG. 1 according to an embodiment addressing high and low temperature conditions of the drug and passively controlling delivery according to temperature.

Further embodiments of a method of operation of the device are illustrated in FIG. 17. These embodiments differ from the preceding embodiments in that a lock is not activated in all circumstances. Accordingly, as illustrated in FIG. 17, a controller according to may determine (or in the case of an electrical embodiment, may be programmed to determine) if the temperature of a drug disposed in a reservoir exceeds an upper limit at block 560. If the temperature exceeds the upper limit, the controller may activate an output device at least once at block 562 (e.g., to alert the use that the temperature of the drug is too high for safety) and place the lock in the locked state at block 564. If the temperature is below the upper limit, the controller may determine (or may be programmed to determine) if the temperature of a drug disposed in the reservoir is below a lower limit at block 566, and if the temperature is below the lower limit, may activate the output device at least once at block 568 (e.g., to alert the user that the temperature of the drug is too low for safety, for comfortable delivery and/or for predictable delivery). According to indicia (e.g., instructions) marked on the external surface of the device (e.g. a cover), for example, the user is informed that upon activation of the output device, the user is to wait a period of time (e.g., five, ten or twenty minutes) before operating the device. However, as indicated at block 570, the device will not be locked and will be operational even after the output device is activated at block 568.

The presumption underlying such an embodiment as is illustrated in FIG. 17 is similar to that underlying the embodiment of FIG. 3: if a sufficient amount of time is permitted to elapse, the heat from the surroundings will increase the temperature of the drug or sensitive component above the lower temperature threshold. Unlike the embodiment in FIG. 3, no lock is activated to prevent use of the system. Optionally, the embodiment of the method according to FIG. 17 may be further simplified by omitting the step at block 564, such that the output device is activated to alert the user to the fact that the drug or temperature-sensitive component has exceeded the upper temperature threshold. According to such an embodiment, the activation of the output device at block 562 may differ from the activation of the output device at block 568, so that the user may differentiate between the two alerts. Moreover, it may be that the device will be permitted to operate after the activation of the output device either at block 562 or at block 568.

Having described the structure and operation of the device, exemplary drugs, medicaments or pharmaceutical products to be contained with the reservoir are discussed below.

For example, the drug delivery device or more specifically the reservoir of the device may be filled with colony stimulating factors, such as G-CSF. Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publ. Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publ. Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; US Publ. Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publ. Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publ. No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO: 2 as set forth therein in FIG. 2 and/or the heavy chain of SEQ ID NO:4, as set forth therein in FIG. 4, each of which is individually and specifically incorporated by reference herein in its entirety fully as disclosed in the foregoing Publication;

Myostatin binding proteins, peptibodies, and related proteins, and the like, including myostatin specific peptibodies, particularly those described in US Publ. No. 2004/0181033 and PCT Publ. No. WO 2004/058988, which are incorporated by reference herein in their entirety particularly in parts pertinent to myostatin specific peptibodies, including but not limited to peptibodies of the mTN8-19 family, including those of SEQ ID NOS: 305-351, including TN8-19-1 through TN8-19-40, TN8-19 con1 and TN8-19 con2; peptibodies of the mL2 family of SEQ ID NOS: 357-383; the mL15 family of SEQ ID NOS: 384-409; the mL17 family of SEQ ID NOS: 410-438; the mL20 family of SEQ ID NOS: 439-446; the mL21 family of SEQ ID NOS: 447-452; the mL24 family of SEQ ID NOS: 453-454; and those of SEQ ID NOS: 615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publ. No. WO 2005/047331 or PCT Appl. No. PCT/US2004/37242 and in US Publ. No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publ. No. 2004/097712A1, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned U.S. publication;

Ang2 specific antibodies, peptibodies, and related proteins, and the like, including but not limited to those described in PCT Publ. No. WO 03/057134 and U.S. Publ No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publ. No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AbIA1; AbIF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in US Publ. No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publ. No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing International Publication;

Also among non-limiting examples of anti-IGF-1R antibodies for use in the methods and compositions of the present invention are each and all of those described in:

(i) US Publ. No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publ. No. WO 06/138729 (published Dec. 28, 2006) and WO 05/016970 (published Feb. 24, 2005), and Lu et al., 2004, J Biol. Chem. 279:2856-65, including but not limited to antibodies 2F8, A12, and IMC-A12 as described therein;

(iii) PCT Publ. No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) US Publ. No. 2005/0084906 (published Apr. 21, 2005), including but not limited to antibody 7C10, chimaeric antibody C7C10, antibody h7C10, antibody 7H2M, chimaeric antibody*7C10, antibody GM 607, humanized antibody 7C10 version 1, humanized antibody 7C10 version 2, humanized antibody 7C10 version 3, and antibody 7H2HM, as described therein;

(v) US Publ. Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al., 2003, Cancer Res. 63:5073-83, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), US Publ. Nos. 2005/0244408 (published Nov. 30, 2005) and 2004/0086503 (published May 6, 2004), and Cohen, et al., 2005, Clinical Cancer Res. 11:2063-73, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) US Publ. Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) US Publ. No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publ. No. 2008/0166352 and PCT Publ. No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing U.S. Publication;

IL-15 specific antibodies, peptibodies, and related proteins, and the like, such as, in particular, humanized monoclonal antibodies, particularly antibodies such as those disclosed in U.S. Publ. Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in US Publ. No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing US Publication and in Thakur et al., Mol. Immunol. 36:1107-1115 (1999). In addition, description of the properties of these antibodies provided in the foregoing US publication is also incorporated by reference herein in its entirety. Specific antibodies include those having the heavy chain of SEQ ID NO: 17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing US Publication. A specific antibody contemplated is antibody 1119 as disclosed in foregoing US Publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publ. Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing US Publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in US Publ. No. 2005/0118643 and PCT Publ. No. WO 2005/017107, huL2G7 described in U.S. Pat. No. 7,220,410 and OA-5d5 described in U.S. Pat. Nos. 5,686,292 and 6,468,529 and in PCT Publ. No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in US Publ. No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and US Publ. No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publ. No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO: 8 and a light chain variable region having SEQ ID NO: 6 as disclosed in the International Publication;

c-Kit specific antibodies, peptibodies, related proteins, and the like, including but not limited to those described in Publ. No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. application Ser. No. 11/086,289, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP 1Ib/IIia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Rα mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβmAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9), e.g. U.S. Pat. No. 8,030,547, U.S. Ser. No. 13/469,032, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223, 593 and 7,537,924); OncoVEXGALV/CD (U.S. Pat. No. 7,981,669); OrienX010 (Lei et al., 2013, World Journal of Gastroenterology, 19:5138-5143); G207, 1716; NV1020; NV12023; NV1034 and NV1042 (Vargehes et al. 2002, Cancer Gene Ther, 2002, 9 (12): 967-978).

Also included are TIMPs. TIMPs are endogenous tissue inhibitors of metalloproteinases (TIMPs) and are important in many natural process. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. 61/782,613, U.S. 61/798,160, U.S. 61/802,988, and US 61/94,067.

Also included are antagonistic antibodies for human calcitonin gene-related peptide (CGRP) receptor and bispecific antibody molecule that target the CGRP receptor and other headache targets. Further information concerning these molecule can be found in WO2A075238A1.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT/2013/075773.

Although the preceding text sets forth a detailed description of different embodiments of the invention, it should be understood that the legal scope of the invention is defined by the words of the claims set forth at the end of this patent. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

We claim:

1. A drug delivery system comprising:
a reservoir adapted to contain a drug;
a drug delivery device coupled to the reservoir to deliver the drug from the reservoir, and comprising a lock having a locked state wherein delivery of the drug from the reservoir is limited and an unlocked state wherein delivery of the drug from the reservoir is not limited;
a temperature sensor;
an output device configured to visually and/or audibly alert a user to a change in an operational state of the drug delivery system; and
a controller coupled to the lock, the temperature sensor, and the output device,
the controller being programmed:
(a) to determine if the temperature of the drug disposed in the reservoir exceeds an upper limit, and if the temperature exceeds the upper limit, to activate the output device at least once to alert the user that the temperature exceeds the upper limit and to place the lock in the locked state;
(b) to determine if the temperature of the drug disposed in the reservoir is below a lower limit, and if the temperature is below the lower limit, to activate the output device at least once to alert the user that the temperature is too low for delivery and to place the lock in the locked state; and
(c) to determine if the temperature of the drug is between the upper limit and the lower limit subsequent to (b), and if the temperature is between the upper limit and the lower limit, to place the lock in the unlocked state.

2. The drug delivery system according to claim 1, wherein the reservoir is adapted to be removed from the drug delivery system, and the controller is programmed to determine if the reservoir has been removed and replaced with another reservoir adapted to contain another drug subsequent to (a), and if the reservoir has been removed and replaced with another reservoir, to place the lock in the unlocked state.

3. The drug delivery system according to claim 1, further comprising a heater coupled to the controller and proximate to at least one of the reservoir and the drug delivery device, the controller programmed to activate the heater if the temperature of the drug is below the lower limit, and to deactivate the heater if the temperature of the drug is between the upper and lower limits.

4. The drug delivery system according to claim 3, wherein the heater comprises at least one of an electrical heater, a chemical heater, and a selectable coupling to a heat source.

5. The drug delivery system according to claim 4, wherein the electrical heater comprises at least one of a resistive heater and a thermoelectric heater.

6. The drug delivery system according to claim 4, wherein the heat source comprises the controller.

7. The drug delivery system according to claim 1, wherein the controller is programmed to determine if temperature sensor is accurate prior to determining if the temperature of the drug disposed in the reservoir is above the upper limit, below the lower limit, or between the upper and lower limits.

8. The drug delivery system according to claim 7, wherein the controller is programmed to adjust a determination of a temperature if the temperature sensor is not accurate.

9. The drug delivery system according to claim 1, wherein the reservoir comprises a pre-filled container.

10. The drug delivery system according to claim 9, wherein the pre-filled container is a pre-filled syringe or a pre-filled cartridge.

11. The drug delivery system according to claim 1, wherein the reservoir comprises an opening and a plunger moveable within the reservoir relative to the opening to force drug out of the reservoir through the opening, and the drug delivery device comprises a plunger arm having a first end in contact with the plunger, and an actuator coupled to the plunger arm.

12. The drug delivery system according to claim 11, wherein the actuator comprises an assembly of an electric motor coupled to the plunger arm and a battery coupled to the electric motor.

13. The drug delivery system according to claim 11, wherein the reservoir comprises a cannula in fluid communication with the opening.

14. The drug delivery system according to claim 1, wherein the temperature sensor comprises at least one of a resistance temperature detector, a thermocouple, an infrared thermopile, and an assembly comprising a thermally-sensitive label and an optical detector.

15. The drug delivery system according to claim 1, wherein the temperature sensor is on-board the controller.

16. The drug delivery system according to claim 1, wherein the reservoir comprises a cannula in fluid communication with the reservoir, and the temperature sensor is coupled to the cannula.

17. The drug delivery system according to claim 16, wherein the cannula comprises a needle.

18. The drug delivery system according to claim 1, wherein the drug or medicament is disposed in the reservoir, and the reservoir comprises an opening and a plunger moveable within the reservoir relative to the opening to force drug out of the reservoir through the opening, and the temperature sensor is attached to the plunger.

19. The drug delivery system according to claim 18, wherein the temperature sensor is in direct contact with the drug.

20. The drug delivery system according to claim 19, wherein the temperature sensor is disposed on an inner surface of the plunger in direct contact with the drug.

21. The drug delivery system according to claim 18, wherein the temperature sensor is not in direct contact with the drug.

22. The drug delivery system according to claim 21, wherein the temperature sensor is disposed within the plunger.

23. The drug delivery system according to claim 1, wherein the output device comprises at least one of a light and a speaker.

24. The drug delivery system according to claim 1, wherein the drug or medicament is disposed in the reservoir.

25. The drug delivery system of claim 24, wherein the drug or medicament disposed in the reservoir comprises (a) a monoclonal antibody (IgG) that binds human Proprotein Convertase Subtilisin/Kexin Type 9 (PCSK9), (b) a colony stimulating factor, or (c) a G-CSF.

26. A drug delivery system comprising:
a reservoir adapted to contain a drug;
a drug delivery device coupled to the reservoir to deliver the drug from the reservoir, and comprising at least one temperature-sensitive component and a lock having a locked state wherein delivery of the drug from the reservoir is limited and an unlocked state wherein delivery of the drug from the reservoir is not limited;
a temperature sensor;
an output device configured to visually and/or audibly alert a user to a change in an operational state of the drug delivery system; and
a controller coupled to the lock, the temperature sensor, and the output device,
the controller being programmed:
(a) to determine if the temperature of the at least one temperature-sensitive component exceeds an upper limit, and if the temperature exceeds the upper limit, to activate the output device at least once to alert the user that the temperature exceeds the upper limit and to place the lock in the locked state;
(b) to determine if the temperature of the at least one temperature-sensitive component is below a lower limit, and if the temperature is below the lower limit, to activate the output device at least once to alert the user that the temperature is too low for delivery and to place the lock in the locked state; and
(c) to determine if the temperature of the at least one temperature-sensitive component is between the upper limit and the lower limit subsequent to (b), and if the temperature is between the upper limit and the lower limit, to place the lock in the unlocked state.

27. The drug delivery system according to claim 26, wherein the at least one temperature-sensitive component comprises a battery.

28. The drug delivery system according to claim 26, wherein the drug or medicament is disposed in the reservoir.

29. The drug delivery system of claim 28, wherein the drug or medicament disposed in the reservoir comprises (a) a monoclonal antibody (IgG) that binds human Proprotein Convertase Subtilisin/Kexin Type 9 (PCSK9), (b) a colony stimulating factor, or (c) a G-CSF.

30. The drug delivery system according to claim 26, wherein the output device comprises at least one of a light and a speaker.

31. A drug delivery system comprising:
a reservoir adapted to contain a drug;
a drug delivery device coupled to the reservoir to deliver the drug in the reservoir,
the drug delivery device including a lock having a locked state wherein delivery of the drug from the reservoir is limited and an unlocked state wherein delivery of the drug from the reservoir is not limited;
a temperature sensor;
an output device configured to visually and/or audibly alert a user to a change in an operational state of the drug delivery system; and
a controller coupled to the lock, the temperature sensor, and the output device,
the controller being programmed:
(a) to determine if the temperature of the drug disposed in the reservoir exceeds an upper limit, and if the temperature exceeds the upper limit, to activate the output device at least once to alert the user that the temperature exceeds the upper limit and to place the lock in the locked state;
(b) to determine if the temperature of the drug disposed in the reservoir is below a lower limit, and if the temperature is below the lower limit, to activate the output device at least once to alert the user that the temperature is too low for delivery and to place the lock in the locked state; and
(c) to determine if a particular time period has elapsed subsequent to (b), and if the particular time period has elapsed, to place the lock in the unlocked state.

32. The drug delivery system according to claim 31, wherein the drug or medicament is disposed in the reservoir.

33. The drug delivery system of claim 32, wherein the drug or medicament disposed in the reservoir comprises (a) a monoclonal antibody (IgG) that binds human Proprotein Convertase Subtilisin/Kexin Type 9 (PCSK9), (b) a colony stimulating factor, or (c) a G-CSF.

34. The drug delivery system according to claim 31, wherein the output device comprises at least one of a light and a speaker.

35. A drug delivery system comprising:
a reservoir adapted to contain a drug;
a drug delivery device coupled to the reservoir to deliver the drug from the reservoir, and comprising a lock having a locked state wherein delivery of the drug from the reservoir is limited and an unlocked state wherein delivery of the drug from the reservoir is not limited;
an output device configured to visually and/or audibly alert a user to a change in an operational state of the drug delivery system; and
a controller coupled to the lock and the output device, the controller comprising a temperature sensor, and configured to:

(a) to determine if the temperature of the drug disposed in the reservoir is below a lower limit, and if the temperature is below the lower limit, to activate the output device at least once to alert the user that the temperature is too low for delivery and to place the lock in the locked state; and (b) to determine if the temperature of the drug is between an upper limit and the lower limit subsequent to (a), and if the temperature is between the upper limit and the lower limit, to place the lock in the unlocked state.

36. The drug delivery system according to claim 35, wherein the drug or medicament is disposed in the reservoir.

37. The drug delivery system of claim 36, wherein the drug or medicament disposed in the reservoir comprises (a) a monoclonal antibody (IgG) that binds human Proprotein Convertase Subtilisin/Kexin Type 9 (PCSK9), (b) a colony stimulating factor, or (c) a G-CSF.

38. The drug delivery system according to claim 35, wherein the output device comprises at least one of a light and a speaker.

39. A method of delivering a drug product, the method comprising:

providing a drug delivery system comprising:
- a reservoir adapted to contain a drug;
- a drug delivery device coupled to the reservoir to deliver the drug from the reservoir, and comprising a lock having a locked state wherein delivery of the drug from the reservoir is limited and an unlocked state wherein delivery of the drug from the reservoir is not limited;
- a temperature sensor;
- an output device configured to visually and/or audibly alert a user to a change in an operational state of the drug delivery system; and
- a controller coupled to the lock, the temperature sensor, and the output device, the controller being programmed:
  (a) to determine if the temperature of the drug disposed in the reservoir exceeds an upper limit, and if the temperature exceeds the upper limit, to activate the output device at least once to alert the user that the temperature exceeds the upper limit and to place the lock in the locked state;
  (b) to determine if the temperature of the drug disposed in the reservoir is below a lower limit, and if the temperature is below the lower limit, to activate the output device at least once to alert the user that the temperature is too low for delivery and to place the lock in the locked state; and
  (c) to determine if the temperature of the drug is between the upper limit and the lower limit subsequent to (b), and if the temperature is between the upper limit and the lower limit, to place the lock in the unlocked state; and providing instructions to a user of the drug delivery system that if the output device is activated, to operate the drug delivery system only after a period of time has elapsed after the output device has been activated.

40. The method according to claim 39, wherein providing instructions comprises providing one or more indicia on a cover of the drug delivery system that conveys to the user that that if the output device is activated, to operate the drug delivery system only after a period of time has elapsed after the output device has been activated.

* * * * *